(12) United States Patent
Dunn

(10) Patent No.: US 9,421,132 B2
(45) Date of Patent: Aug. 23, 2016

(54) NEGATIVE PRESSURE WOUND CLOSURE DEVICE

(71) Applicant: University of Massachusetts, Boston, MA (US)

(72) Inventor: Raymond Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 65 days.

(21) Appl. No.: 13/942,493

(22) Filed: Jul. 15, 2013

(65) Prior Publication Data

US 2014/0180225 A1    Jun. 26, 2014

Related U.S. Application Data

(63) Continuation-in-part of application No. 13/365,615, filed on Feb. 3, 2012, now Pat. No. 9,226,737.

(60) Provisional application No. 61/439,525, filed on Feb. 4, 2011, provisional application No. 61/672,173, filed on Jul. 16, 2012, provisional application No. 61/679,982, filed on Aug. 6, 2012, provisional application No. 61/779,900, filed on Mar. 13, 2013.

(51) Int. Cl.
*A61M 1/00* (2006.01)
*A61F 13/00* (2006.01)
*A61B 17/08* (2006.01)

(52) U.S. Cl.
CPC ........ *A61F 13/00068* (2013.01); *A61M 1/0088* (2013.01); *A61B 17/08* (2013.01); *A61B 2017/081* (2013.01); *A61F 2013/0054* (2013.01); *A61F 2013/00174* (2013.01); *A61F 2013/00536* (2013.01); *A61F 2013/00544* (2013.01); *A61F 2013/00548* (2013.01)

(58) Field of Classification Search
CPC ......... A61F 13/00; A61F 13/02; A61F 13/04; A61M 1/00; A61M 27/00
See application file for complete search history.

(56) References Cited

U.S. PATENT DOCUMENTS

| 3,194,239 A | 7/1965 | Sullivan |
| 5,415,715 A | 5/1995 | Delage et al. |
| 5,636,643 A | 6/1997 | Argenta et al. |
| 5,960,497 A | 10/1999 | Castellino et al. |
| 6,080,168 A | 6/2000 | Levin et al. |

(Continued)

FOREIGN PATENT DOCUMENTS

| DE | 10 2005 007016 | 8/2006 |
| EP | 1320342 A1 | 6/2003 |

(Continued)

OTHER PUBLICATIONS

English translation of specfication, WO 2011/023384 A1 (2011).*

(Continued)

*Primary Examiner* — Melanie Hand
(74) *Attorney, Agent, or Firm* — Knobbe, Martens, Olson & Bear LLP

(57) ABSTRACT

The present invention relates to a negative pressure wound closure system and methods for using such a system. Preferred embodiments of the invention facilitate closure of the wound by preferentially contracting to provide for movement of the tissue. Preferred embodiments can utilize tissue grasping elements to apply a wound closing force to the tissue.

23 Claims, 21 Drawing Sheets

(56) References Cited

U.S. PATENT DOCUMENTS

| | | |
|---|---|---|
| 6,086,591 A | 7/2000 | Bojarski |
| 6,142,982 A | 11/2000 | Hunt et al. |
| 6,553,998 B2 | 4/2003 | Heaton et al. |
| 6,685,681 B2 | 2/2004 | Lockwood et al. |
| 6,695,823 B1 | 2/2004 | Lina et al. |
| 6,712,830 B2 | 3/2004 | Esplin |
| 6,767,334 B1 | 7/2004 | Randolph |
| 6,770,794 B2 | 8/2004 | Fleischmann |
| 6,814,079 B2 | 11/2004 | Heaton et al. |
| 6,893,452 B2 | 5/2005 | Jacobs |
| 6,936,037 B2 | 8/2005 | Bubb |
| 6,951,553 B2 | 10/2005 | Bubb et al. |
| 6,994,702 B1 | 2/2006 | Johnson |
| 7,004,915 B2 | 2/2006 | Boynton et al. |
| 7,025,755 B2 | 4/2006 | Epstein |
| 7,070,584 B2 | 7/2006 | Johnson et al. |
| 7,117,869 B2 | 10/2006 | Heaton et al. |
| 7,128,735 B2 | 10/2006 | Weston |
| 7,144,390 B1 | 12/2006 | Hannigan et al. |
| 7,153,312 B1 | 12/2006 | Torrie et al. |
| 7,156,862 B2 | 1/2007 | Jacobs et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| 7,198,046 B1 | 4/2007 | Argenta et al. |
| 7,216,651 B2 | 5/2007 | Argenta et al. |
| D544,092 S | 6/2007 | Lewis |
| 7,262,174 B2 | 8/2007 | Jiang et al. |
| 7,279,612 B1 | 10/2007 | Heaton et al. |
| 7,315,183 B2 | 1/2008 | Hinterscher |
| 7,351,250 B2 | 4/2008 | Zamierowski |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,413,571 B2 | 8/2008 | Zamierowski |
| 7,438,705 B2 | 10/2008 | Karpowicz et al. |
| 7,494,482 B2 | 2/2009 | Orgill et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,615,036 B2 | 11/2009 | Joshi et al. |
| 7,618,382 B2 | 11/2009 | Vogel et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,683,667 B2 | 3/2010 | Kim |
| 7,699,823 B2 | 4/2010 | Haggstrom et al. |
| 7,699,830 B2 | 4/2010 | Martin |
| 7,699,831 B2 | 4/2010 | Bengtson et al. |
| 7,700,819 B2 | 4/2010 | Ambrosio et al. |
| 7,708,724 B2 | 5/2010 | Weston |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,754,937 B2 | 7/2010 | Boehringer et al. |
| 7,776,028 B2 | 8/2010 | Miller et al. |
| 7,777,522 B2 | 8/2010 | Yang |
| 7,779,625 B2 | 8/2010 | Joshi et al. |
| D625,801 S | 10/2010 | Pidgeon et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,857,806 B2 | 12/2010 | Karpowicz et al. |
| 7,896,856 B2 | 3/2011 | Petrosenko et al. |
| 7,909,805 B2 | 3/2011 | Weston |
| 7,942,866 B2 | 5/2011 | Radl et al. |
| 7,951,124 B2 | 5/2011 | Boehringer et al. |
| 7,981,098 B2 | 7/2011 | Boehringer et al. |
| 8,030,534 B2 | 10/2011 | Radl et al. |
| 8,062,272 B2 | 11/2011 | Weston |
| 8,062,295 B2 | 11/2011 | McDevitt et al. |
| 8,062,331 B2 | 11/2011 | Zamierowski |
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,197,467 B2 | 6/2012 | Heaton et al. |
| 8,207,392 B2 | 6/2012 | Haggstrom et al. |
| 8,235,955 B2 | 8/2012 | Blott et al. |
| 8,273,105 B2 | 9/2012 | Cohen et al. |
| 8,353,931 B2 | 1/2013 | Stopek et al. |
| 8,399,730 B2 | 3/2013 | Kazala, Jr. et al. |
| 8,444,392 B2 | 5/2013 | Turner et al. |
| 8,447,375 B2 | 5/2013 | Shuler |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,562,576 B2 | 10/2013 | Hu et al. |
| 8,608,776 B2 | 12/2013 | Coward et al. |
| 8,622,981 B2 | 1/2014 | Hartwell et al. |
| 8,632,523 B2 | 1/2014 | Eriksson et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,721,629 B2 | 5/2014 | Hardman et al. |
| 8,747,375 B2 | 6/2014 | Barta et al. |
| 8,791,315 B2 | 7/2014 | Lattimore et al. |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Zimnitsky et al. |
| 8,936,618 B2 | 1/2015 | Sealy et al. |
| 2001/0029956 A1 | 10/2001 | Argenta et al. |
| 2002/0022861 A1 | 2/2002 | Jacobs et al. |
| 2002/0161346 A1 | 10/2002 | Lockwood et al. |
| 2003/0065360 A1 | 4/2003 | Jacobs et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0243073 A1 | 12/2004 | Lockwood et al. |
| 2005/0119694 A1 | 6/2005 | Jacobs et al. |
| 2005/0182445 A1 | 8/2005 | Zamierowski |
| 2005/0209574 A1 | 9/2005 | Boehringer et al. |
| 2005/0222613 A1 | 10/2005 | Ryan |
| 2005/0258887 A1 | 11/2005 | Ito |
| 2006/0058842 A1 | 3/2006 | Wilke et al. |
| 2006/0064124 A1 | 3/2006 | Zhu et al. |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2007/0032755 A1 | 2/2007 | Walsh |

(56) References Cited

U.S. PATENT DOCUMENTS

| | | |
|---|---|---|
| 2007/0032763 A1 | 2/2007 | Vogel |
| 2007/0038172 A1 | 2/2007 | Zamierowski |
| 2007/0118096 A1 | 5/2007 | Smith et al. |
| 2007/0123816 A1 | 5/2007 | Zhu et al. |
| 2007/0149910 A1 | 6/2007 | Zocher |
| 2007/0185463 A1 | 8/2007 | Mulligan |
| 2007/0213597 A1 | 9/2007 | Wooster |
| 2007/0219513 A1 | 9/2007 | Lina et al. |
| 2007/0265585 A1 | 11/2007 | Joshi et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0167593 A1 | 7/2008 | Fleischmann |
| 2008/0177253 A1 | 7/2008 | Boehringer et al. |
| 2008/0287973 A1 | 11/2008 | Aster et al. |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299303 A1 | 12/2009 | Seegert |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0087854 A1 | 4/2010 | Stopek et al. |
| 2010/0100022 A1 | 4/2010 | Greener et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0305490 A1 | 12/2010 | Coulthard et al. |
| 2010/0318046 A1 | 12/2010 | Boehringer et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0054283 A1 | 3/2011 | Shuler |
| 2011/0054365 A1 | 3/2011 | Greener |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0105963 A1 | 5/2011 | Hu et al. |
| 2011/0106026 A1 | 5/2011 | Wu et al. |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0213287 A1 | 9/2011 | Lattimore et al. |
| 2011/0224631 A1 | 9/2011 | Simmons |
| 2011/0224632 A1 | 9/2011 | Zimitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez Canada |
| 2011/0264138 A1 | 10/2011 | Avelar et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0313374 A1 | 12/2011 | Lockwood et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Goulthard |
| 2012/0029449 A1 | 2/2012 | Khosrowshahi |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0136326 A1 | 5/2012 | Croizat et al. |
| 2012/0143113 A1 | 6/2012 | Robinson et al. |
| 2012/0143158 A1 | 6/2012 | Yang et al. |
| 2012/0144989 A1 | 6/2012 | Du Plessis et al. |
| 2012/0150133 A1 | 6/2012 | Heaton et al. |
| 2012/0157942 A1 | 6/2012 | Weston |
| 2012/0165764 A1 | 6/2012 | Allen et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1 | 8/2012 | Dunn |
| 2012/0220968 A1 | 8/2012 | Confalone et al. |
| 2012/0222687 A1 | 9/2012 | Czajka, Jr. et al. |
| 2012/0277773 A1 | 11/2012 | Sargeant et al. |
| 2012/0302440 A1 | 11/2012 | Theliander et al. |
| 2013/0096518 A1 | 4/2013 | Hall et al. |
| 2013/0110058 A1 | 5/2013 | Adie et al. |
| 2013/0131564 A1 | 5/2013 | Locke et al. |
| 2013/0138054 A1 | 5/2013 | Fleischmann |
| 2013/0150814 A1 | 6/2013 | Buan |
| 2013/0197457 A1 | 8/2013 | Kazala et al. |
| 2013/0245527 A1 | 9/2013 | Croizat et al. |
| 2013/0253401 A1 | 9/2013 | Locke et al. |
| 2014/0068914 A1 | 3/2014 | Coward et al. |
| 2014/0088455 A1 | 3/2014 | Christensen et al. |
| 2014/0094730 A1 | 4/2014 | Greener |
| 2014/0163415 A1 | 6/2014 | Zaiken et al. |
| 2014/0194836 A1 | 7/2014 | Kazala et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2015/0005722 A1 | 1/2015 | Hu et al. |
| 2015/0025484 A1 | 1/2015 | Simmons et al. |
| 2015/0065968 A1 | 3/2015 | Sealy et al. |
| 2015/0080947 A1 | 3/2015 | Greener |
| 2015/0112290 A1 | 4/2015 | Dunn |
| 2015/0112311 A1 | 4/2015 | Hammond et al. |
| 2015/0119865 A1 | 4/2015 | Barta et al. |
| 2015/0148760 A1 | 5/2015 | Dodd et al. |
| 2015/0150729 A1 | 6/2015 | Dagger et al. |

FOREIGN PATENT DOCUMENTS

| | | |
|---|---|---|
| EP | 2094211 A1 | 9/2009 |
| EP | 2 279 016 | 2/2011 |
| EP | 2368523 A1 | 9/2011 |
| EP | 2404571 A1 | 1/2012 |
| EP | 2404626 A2 | 1/2012 |
| EP | 2 341 955 | 12/2012 |
| EP | 2 563 421 | 3/2013 |

(56) References Cited

FOREIGN PATENT DOCUMENTS

| | | |
|---|---|---|
| EP | 2 567 717 | 3/2013 |
| EP | 2594299 A2 | 5/2013 |
| EP | 2 601 984 A2 | 6/2013 |
| EP | 2 623 137 | 8/2013 |
| EP | 2 367 517 | 9/2013 |
| GB | 2423019 | 8/2006 |
| WO | WO 2004/018020 | 3/2004 |
| WO | WO 2006/041496 | 4/2006 |
| WO | WO 2006/087021 | 8/2006 |
| WO | WO 2008/064502 | 6/2008 |
| WO | WO 2008/104609 | 9/2008 |
| WO | 2009019495 A1 | 2/2009 |
| WO | 2009/071926 A1 | 6/2009 |
| WO | 2009071933 A2 | 6/2009 |
| WO | 2009/112848 A1 | 9/2009 |
| WO | 2009/114624 A2 | 9/2009 |
| WO | WO 2009112062 A1 * 9/2009 ............. A61B 17/34 | |
| WO | 2009156709 A1 | 12/2009 |
| WO | 2010079359 A1 | 7/2010 |
| WO | WO 2010/075180 | 7/2010 |
| WO | WO 2010/078349 | 7/2010 |
| WO | 2010092334 A1 | 8/2010 |
| WO | 2010/097570 A1 | 9/2010 |
| WO | WO 2010/147535 | 12/2010 |
| WO | WO 2011/023384 | 3/2011 |
| WO | 2011087871 A2 | 7/2011 |
| WO | 2011091169 A1 | 7/2011 |
| WO | WO 2011/106722 | 9/2011 |
| WO | WO 2011/115908 | 9/2011 |
| WO | 2011/137230 A1 | 11/2011 |
| WO | 2011135286 A1 | 11/2011 |
| WO | 2011135287 A1 | 11/2011 |
| WO | 2012/021553 A1 | 2/2012 |
| WO | 2012038727 A2 | 3/2012 |
| WO | 2012/082716 A2 | 6/2012 |
| WO | 2012087376 A1 | 6/2012 |
| WO | WO 2012/082876 | 6/2012 |
| WO | WO 2012/106590 | 8/2012 |
| WO | WO 2012/112204 | 8/2012 |
| WO | 2012/136707 A1 | 10/2012 |
| WO | 2012156655 A1 | 11/2012 |
| WO | 2012168678 A1 | 12/2012 |
| WO | WO 2013/012381 | 1/2013 |
| WO | WO 2013/043258 | 3/2013 |
| WO | 2013/074829 A1 | 5/2013 |
| WO | PCT/IB2013/002485 | 5/2013 |
| WO | WO 2013/071243 | 5/2013 |
| WO | WO 2013/175309 | 11/2013 |
| WO | WO 2013/175310 | 11/2013 |
| WO | WO 2014/013348 | 1/2014 |
| WO | WO 2014/014842 | 1/2014 |
| WO | WO 2014/014871 | 1/2014 |
| WO | WO 2014/014922 | 1/2014 |
| WO | WO 2014/158526 | 10/2014 |
| WO | WO 2014/165275 | 10/2014 |

OTHER PUBLICATIONS

Kapischke, M. et al., "Self-fixating mesh for the Lichtenstein procedure—a prestudy", Langenbecks Arch Surg (2010), 395 p. 317-322.
U.S. Appl. No. 14/415,470, filed Jan. 16, 2015, Smith & Nephew.
U.S. Appl. No. 14/415,539, filed Jan. 16, 2015, Smith & Nephew.
Hougaard, et al.: "The open abdomen: temporary closure with a modified negative pressure therapy technique," International Wound Journal, 2014 ISSN 1742-4801, pp. 13-16.
International Preliminary Report on Patentability and Written Opinion re PCT/US2013/050558, issued Jan. 20, 2015.

* cited by examiner

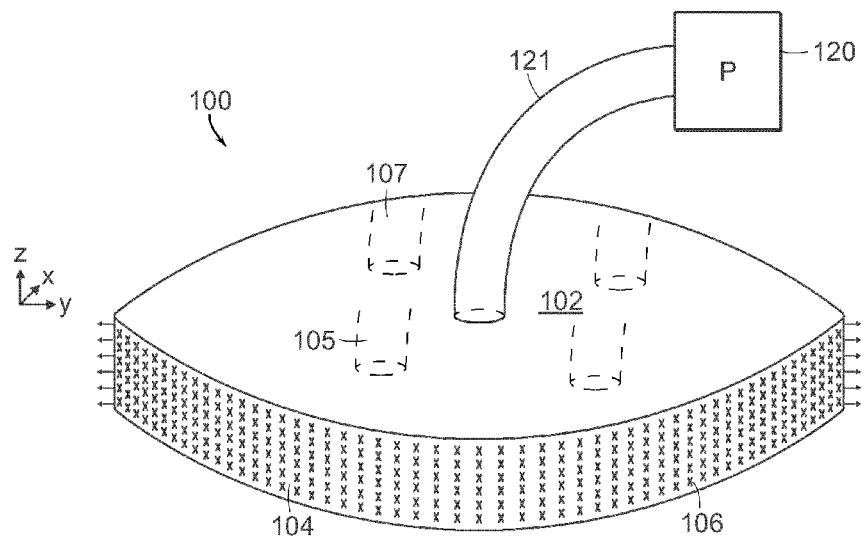
FIG. 1A
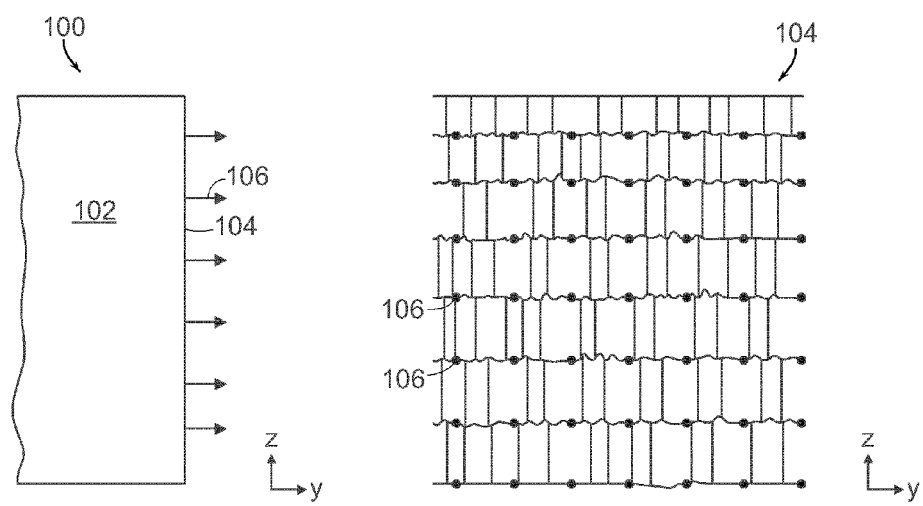
FIG. 1B
FIG. 1C

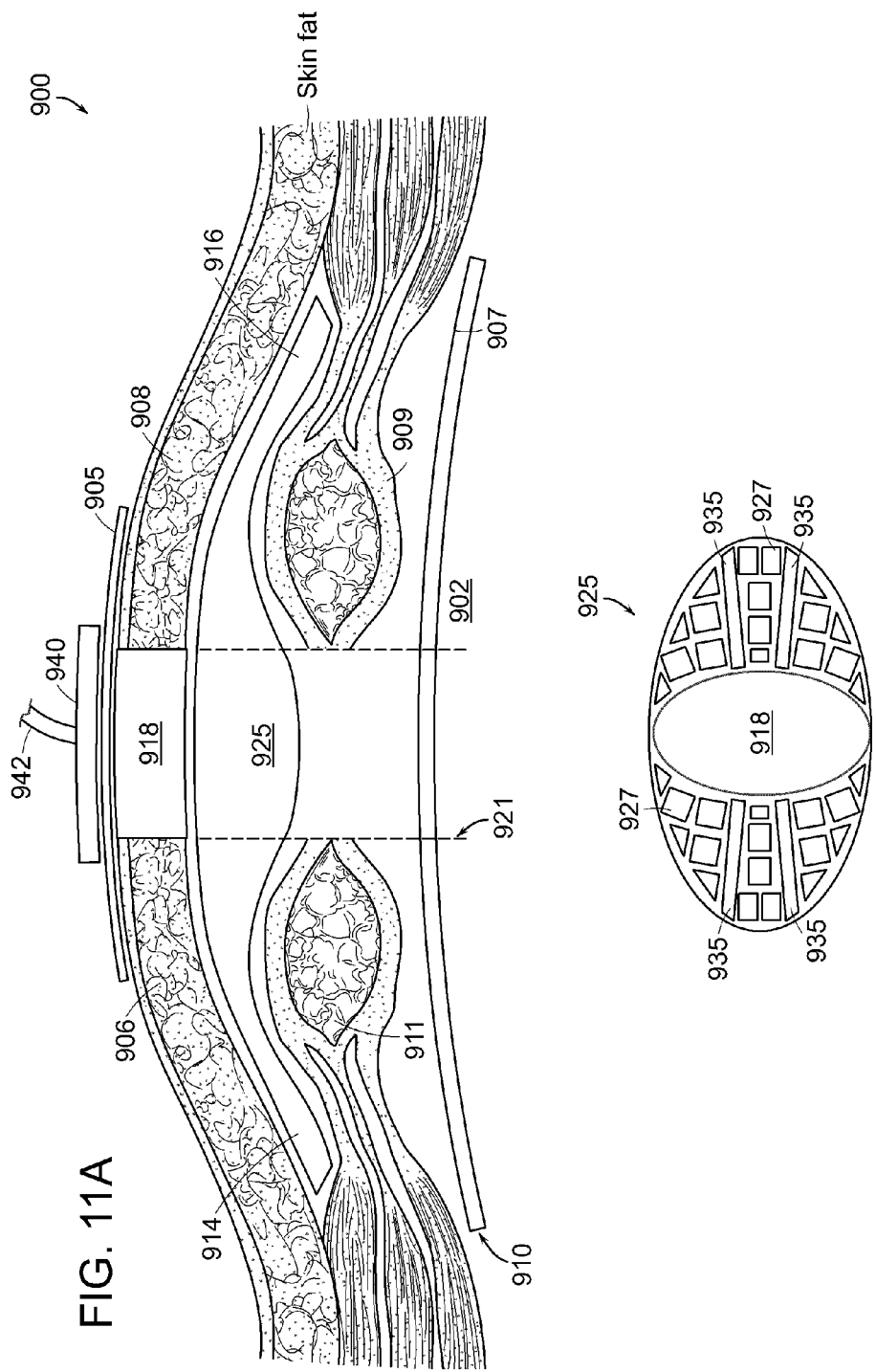

NEGATIVE PRESSURE WOUND CLOSURE DEVICE

CROSS REFERENCE TO RELATED APPLICATIONS

This application is a continuation-in-part of U.S. application Ser. No. 13/365,615, filed Feb. 3, 2012, which claims the benefit of U.S. Application Nos. 61/439,525, filed Feb. 4, 2011. This application also claims the benefit of U.S. Application No. 61/672,173 filed Jul. 16, 2012, U.S. Application No. 61/679,982 filed Aug. 6, 2012, and U.S. Application No. 61/779,900, filed Mar. 13, 2013. The entire contents of the above applications are incorporated herein by reference.

BACKGROUND OF THE INVENTION

A number of techniques have been developed for treatment of wounds, including wounds resulting from accident and wounds resulting from surgery. Often, wounds are closed using sutures or staples. However, inserting these mechanical closure techniques requires making additional punctures or wounds to the skin, which can result in tissue injury and in the case of excess swelling, possible ischemia and tissue loss. Also, mechanical wound closures such as staples and sutures can cause highly-localized stresses at the insertion points that can impede and damage the normal wound healing processes of the skin.

In recent years, there has been increased interest in using negative pressure devices for the treatment of wounds. Negative pressure wound treatment utilizes devices that remove wound fluids by applying negative pressure suction to the wound. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in negative pressure wound therapy are needed to fully realize the benefits of treatment.

SUMMARY OF THE INVENTION

The present invention relates to a negative pressure wound closure device that specifically exerts force at the edges of the wound to facilitate closure of the wound. The device operates to reduce the need for repetitive replacement of wound filler material currently employed and can advance the rate of healing. The device simultaneously uses negative pressure to remove wound fluids and to assist in closure of the wound.

In one embodiment, a negative pressure wound closure device includes a wound filler material that is sized and shaped to fit within a wound opening and which contracts along at least one dimension upon application of a negative pressure to the filler material. The filler material is thus configured to preferentially contract in at least one direction and inhibit contractions in one or more additional directions. Prior negative pressure devices did not assist in wound closure, but were used to drain fluids. By providing for the controlled movement of tissue during the healing process in conjunction with the drainage of fluids from wounds as described in connection with the present invention, a substantial improvement in the rate of healing can be realized. Note that depending on the size of the wound, increased negative pressure can be used.

In another preferred embodiment, a tissue grasping surface extends over an outer peripheral surface of the wound filler material and includes a plurality of tissue anchors that engage the tissue at the wound margin. Upon application of negative pressure, the tissue at the wound margin is displaced to facilitate closure of the wound. A negative pressure source, such as a vacuum pump, is coupled to the wound filler material to provide the negative pressure.

The wound filler material generally comprises a porous material, such as a foam. For embodiments employing tissue anchors, these can be integrally formed in the filler material. In other embodiments, the tissue anchors are provided on a separate covering or film that is secured to the filler material.

In preferred embodiments, the filler material includes a stabilizing structure that enables the material to collapse in at least one first direction and inhibits collapse in at least one second direction. The stabilizing structure can include regions of relatively rigid material surrounded by regions of relatively compressible material. In preferred embodiments, the stabilizing structure is an endoskeleton formed of rigid and/or semi-rigid materials.

In exemplary embodiments, the regions of compressible material may include one or more sections of a compressible material configured, e.g., sized and shaped, for association with one or more surfaces defined by the stabilizing structure. For example, a stabilizing structure may define a top surface, a bottom surface and one or more side surfaces each, of which being associated with a corresponding section of a compressible material. In exemplary embodiments, each section of the compressible material can be configured, e.g., sized and shaped, to match the corresponding surface. Thus, the sections of compressible material cooperate to envelope the stabilizing structure, e.g. to facilitate structural characteristics as described in the present application. In some embodiments, a tissue grasping surface, such as described above, may extend over an outer peripheral surface of the compressible material, e.g. of the side sections of the compressible material that can engage the wound margins of an open wound.

In exemplary embodiments the sections of compressible material can define a plurality of surface features on the inner peripheral surfaces thereof. For example, the sections of compressible material may define an "egg crate" pattern of ridges and valleys. Advantageously, the surface features defined on the inner peripheral surface of the sections of compressible material can be configured for operative association with an inner volume of stabilizing structure. In exemplary embodiments, each surface of the stabilizing structure may define a lattice pattern of stabilizer elements. Thus, the surface features defined on the inner peripheral surface of each section of compressible material may be configured, e.g., patterned, to match the lattice pattern of the corresponding surface of the stabilizer element. In exemplary embodiments, the surface features defined on the inner peripheral surface of each section may provide tensile forces to the stabilizing structure, e.g., during the collapse thereof, to facilitate a structured collapse, e.g., in one or more directions. In some embodiments, the surface features defined on the inner peripheral surface of each section may be configured to impart a pre-selected force profile to the stabilizing structure, e.g., during the collapse thereof. In some embodiments, a pre-selected force profile can control the collapse of the stabilizing structure, e.g., providing for a non-uniform collapse such as by resisting collapse in one or more directions and/or in one or more regions. The shaped wound filler material provides for fluid transport across the device during the application of negative pressure. Consequently, a preferred embodiment provides for continuous contact of wound filler elements to facilitate continuous flow of fluid from the tissue margins and underlying tissue to the fluid exit port(s) for drainage from the wound.

In certain embodiments, the stabilizing structure inhibits the filler material from collapsing along its height dimension, while enabling the filler material to collapse within the plane defined by the wound margins. This is useful in the case of abdominal surgery, for example, in which the surgical incision is along a straight line and opens laterally to form an oval shaped wound. This generally oval shaped wound can extend through muscle and fatty tissue having variable mechanical properties. Wound healing is better served through the use of an oval shaped structure adapted to preferentially collapse towards the original line of incision. In preferred embodiments, the stabilizing structure promotes collapse of the filler material in a manner to effect reapproximation of the wound tissue. Fasciotomy wounds, or other wound dehiscences, or any open wound can be successfully treated using embodiments of the present invention.

The wound closure device can be used to treat wounds in the mediastinum, for pressure ulcers, for wounds in the extremities (arms or legs) etc. The wound closure device can also be used to treat wounds of different shapes, such as circular, square, rectangular or irregularly shaped wounds. A plurality of wound closure elements can be shaped to fit within a wound and can attach together to preferentially close the wound in a desired direction. The different elements can comprise different materials or have different characteristics, such as pore size and/or anchor size and distribution to form a composite structure.

In one embodiment, an endoskeleton stabilizing structure includes a plurality of spaced-apart rigid members forming a cross-hatched configuration. The endoskeleton enables the filler material to collapse along its width dimension and elongate to a smaller degree along its length dimension. In certain embodiments, a plurality of rigid members extend along the height of the filler material and inhibit collapse of the material in its height dimension, for example. According to certain embodiments, the endoskeleton comprises a network of interconnected rigid members that can articulate with respect to one another during collapse of the filler material. The endoskeleton can include truss supports to inhibit tilting motion of the filler material. In some embodiments, the tissue anchors can be integrally formed in the endoskeleton. The endoskeleton can have flexure elements with elastic properties such that the lateral force imparted by the skeleton is a function of displacement. The endoskeleton or frame prevents tilting of the wound closure device during use. The frame can include hollow tubes or cavities that alter the flex characteristics of the frame. The tubes or cavities can be used for the delivery of media into the wound.

A preferred embodiment of the invention utilizes a wound healing device for the treatment of wounds in which seromas can form. The wound healing device can include apertures to provide for tissue contact through the apertures to promote wound healing. The device can include removalable drain elements for the application of negative pressure.

In certain embodiments, the wound filler material includes a smooth bottom surface having micropores to allow the passage of fluid from the wound through the bottom surface and into the device for removal. The micropores can have variable pore size and/or pore density to direct the distribution of vacuum force from the negative pressure source. In some embodiments, the wound filler material can have variable internal pore sizes and/or pore density to direct the distribution of vacuum force.

In one embodiment, a negative pressure wound treatment component for managing and/or removing fluid is coupled to the wound filler material. A single negative pressure source can be used for wound closure and fluid management/drainage. A sliding surface is provided at the interface between the wound closure and fluid management components.

In yet another embodiment, the filler material includes removable portions to adjust the size of the wound closure device. The filler material can be provided with pre-determined cleavage lines for tearing or cutting away portions of the material. In certain embodiments, sets of tissue anchors are embedded in the filler material, and become exposed by removing excess portions of the material.

According to another embodiment, the tissue anchors are provided with a variable force profile. The force profile can vary based on the depth of tissue or the type of tissue engaged. In some embodiments, the force profile of the tissue grasping surface varies around the perimeter of the wound closure device. The force profile is varied, for instance, by varying one or more of the length of the tissue anchors, the shape of the anchors, the materials of the anchors and the density of the anchors.

The present invention also relates to methods of closing a wound using a wound closure device as described above. For example, a linear incision in the skin overlying the abdomen provides access to a surgical site such as the gastrointestinal system of the human or animal body. Following completion, the wound must be treated by negative pressure therapy to facilitate recovery. Thus, a wound closure device in accordance with preferred embodiments of the invention is inserted for wound closure treatment.

In a preferred embodiment, the wound closure device does not include tissue anchors, but instead utilizes a structure having a shape memory such that it expands to fill the wound cavity. Thus, the expanding frame exerts an expansion force when compressed so that the lateral peripheral elements of the device maintain contact with the wound margins around the peripheral surfaces of the wound closure device. The laterally directed outward expansion force is less than the closure force exerted on the tissue upon application of negative pressure that operates to close the wound margins and compress the wound closure device.

By using the negative pressure wound closure device of the invention, patients with large or severe wounds are able to be discharged or engage in rehabilitative physical therapy, changed at home and then brought back to have their wounds simply stitched closed. By improving wound closure treatment and thereby reducing cost, there is an opportunity for these devices to be a significant part of the instruments used for wound care.

A preferred embodiment of the invention uses a wound healing device in combination with a wound closure device for treatment of wounds requiring both components.

BRIEF DESCRIPTION OF THE DRAWINGS

Other features and advantages of the present invention will be apparent from the following detailed description of the invention, taken in conjunction with the accompanying drawings of which:

FIG. 1A is a perspective schematic view of a negative pressure wound closure device.

FIG. 1B is a cross-section view of the tissue grasping surface of the wound closure device.

FIG. 1C is a side view of one embodiment of the tissue grasping surface.

FIG. 11A illustrates a cross sectional view of a wound drain and closure system at a surgical site in accordance with a preferred embodiment of the invention.

FIG. 11B illustrates a top view of a wound closure device and a tissue adhesion device.

DETAILED DESCRIPTION OF THE INVENTION

Figure 1D:
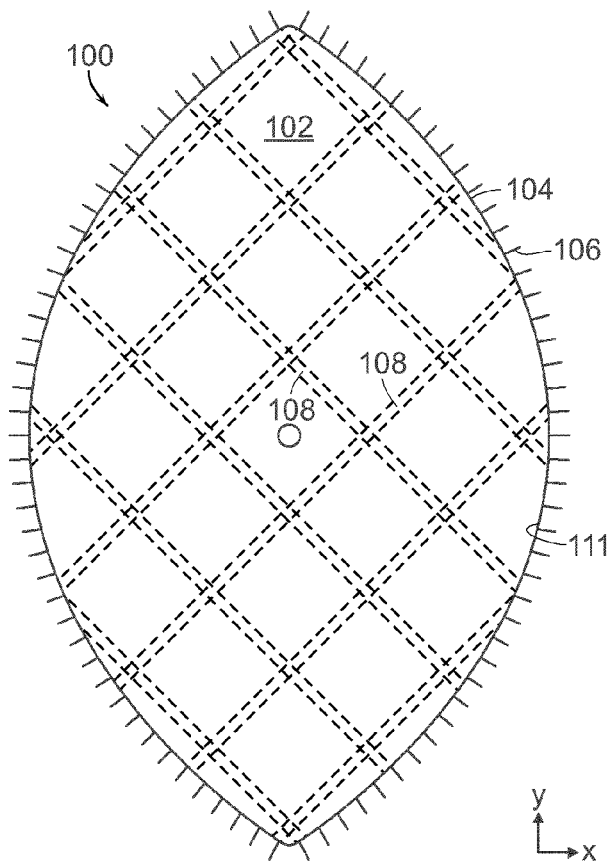
FIG. 1D is a top view of the wound closure device showing x-y stabilizers in phantom.

FIGS. 1A-1F illustrate an embodiment of a wound closure device 100 of the present invention. The device 100 includes a wound filler material 102 that is sized and shaped to fit within a wound opening of a human or animal patient. In preferred embodiments, the filler material 102 is a porous, biocompatible material, such as an open cell polyurethane foam. The filler material 102 is also preferentially collapsible, meaning that its size can be reduced along at least one dimension (e.g., length, width, height) by applying a negative pressure to the filler material 102, while at the same time inhibiting contractions or contracting at a slower rate in another direction. Further details regarding devices and methods of the present invention can be found in U.S. application Ser. No. 13/365,615 filed on Feb. 3, 2012, the entire contents of which is incorporated herein by reference.

Extending over at least one surface of the filler material 102, and preferably extending over an outer perimeter surface of the filler material 102 is a tissue grasping surface 104. In one embodiment, the tissue grasping surface 104 is a flexible covering, such as a mesh film, that is secured to the outer perimeter surface of the filler material 102 and can expand and contract with the expansion and contraction of the filler material 102. In one embodiment, the tissue grasping surface 102 is a mesh film or a composite polyester mesh film, such as the Parietex™ mesh from Covidien (Mansfield, Mass.). The tissue grasping surface 104 includes a plurality of outward-facing tissue anchor elements 106, which in the preferred embodiment are a plurality of closely-spaced barbs, hooks or tissue grasping elements, which can be integrally formed in the mesh film.

FIG. 1B is an edge view of the device 100 showing the tissue grasping elements 106 projecting from the tissue grasping surface 104 on the periphery of the wound filler material 102. FIG. 1C is a side view of one embodiment, in which the tissue grasping surface 104 is formed from a flexible material, in particular, a mesh material. The grasping elements 106 project out from the page in FIG. 1C. The flexible, mesh material of the tissue grasping surface 104 allows the surface to expand and contract as necessary with the expansion and contraction of the underlying wound filler material 102.

In other embodiments, the tissue grasping surface 104 with anchor elements 106 can be integrally formed in the filler material 102. The tissue grasping surface and/or anchor elements can also be formed using a resorbable material.

The tissue anchor elements 106 are preferably provided over an entire outer perimeter surface of the filler material 102. When the filler material 102 is placed within a wound, the anchor elements 106 become buried within the tissue at the wound margins and secure the device 100 within the wound opening. The tissue anchor elements 106 are preferably spread out over the entire surface of the wound margin to provide sufficient strength in the grasping force. The tissue grasping surface 104 is preferably designed to allow the wound closure device 100 to be easily placed but also easily removed and replaced with a new device 100 or other wound dressing as needed (e.g., 2-7 days later). The grasping surface 104 can be configured to have high grasping strength over at least a portion of its surface, but easily removable by, for example, pulling away at an edge. The tissue grasping surface 104 is preferably designed to be removed from a wound without damaging the surrounding tissue. The anchor elements 106 are preferably designed to accommodate various tissue applications, such as muscle, fat, skin and collagen, and various combinations of these. The anchor elements 106 can also be designed to remain securely attached to particular tissues for a selected time period in certain embodiments.

In embodiments in which the grasping surface 104 is formed from a covering on the outer peripheral surface of the filler material 102, the grasping surface can be attached to the filler material 102 using any suitable technique, such as with an adhesive or a mechanical fastening system. In a preferred embodiment, the tissue grasping surface 104 includes filler-grasping anchor elements, which can be barbs, that secure the grasping surface to the filler material. As shown in the cross-section view of FIG. 6, for example, the grasping surface 400 comprises a thin mesh or film having two sets of barbs or similar anchor elements, a first set 410 of outwardly-facing tissue-grasping elements 412 that are designed to project into tissue, and a second set 404 of elements 406 that project into the filler material to secure the grasping surface to the filler material.

Returning to FIGS. 1A-1F, a negative pressure source 120, such as a pump, is coupled to the filler material 102 by a suitable coupling or conduit, such as tube 121. Additional tubes 107 can also be connected through an array of spaced ports 105 in order to spatially distribute the suction force so that the force exerted along the sidewall 104 can be controlled separately from a fluid suction force. The negative pressure source 120 can be activated to apply a negative pressure to the filler material 102. In general, the negative pressure causes a resulting pressure differential which causes the filler material 102 to contract or "collapse." As the filler material 102 contracts, the tissue grasping surface 104 grabs and pulls on the adjacent tissue, which is preferably the tissue around a wound margin, resulting in the displacement of the tissue thereby facilitating the closure of the wound. In a preferred embodiment, the filler material 102 is designed to collapse preferentially in at least one direction. For example, in the embodiment of FIG. 1A, the filler material 102 includes a length and width dimension along the y- and x-axes, respectively, and a height along the z-axis. In order to efficiently transmit the negative pressure to the subcutaneous or other wound margins, it is preferred that the filler material 102 does not collapse centrally in the z-direction (like a pancake), so that the action of the negative pressure works predominantly in the x-y directions, or more particularly, in a two-dimensional plane along the wound margins such as in an open abdomen or fasciotomy. It will be understood that in some embodiments, the plane of the wound margins can be curved, such as when the wound goes around the curve of an abdomen or leg.

Furthermore, in preferred embodiments the filler material 102 is configured to preferentially collapse in length and/or width (i.e., along the x- and y-axes) to reapproximate the tissue at the wound margins Note that certain types of wounds can be treated without the anchor elements described herein.

There are several ways in which the filler material 102 is configured to exhibit preferential collapse characteristics. For example, portions of the filler material 102 can be made from more rigid material than the surrounding material, causing the filler material to preferentially collapse in a particular direction. In one embodiment, the filler material 102 can include a stabilizing endoskeleton made from a suitable rigid material embedded within a "collapsible" filler, such as an open cell foam. Note that the amount of applied negative pressure can be adjustable depending on the size and shape of the wound. Pressures above 125 mm, to as much as 250 mm or more can be used to assist in wound closure. The pressure can be reduced over time as the wound contracts.

Figure 1E:
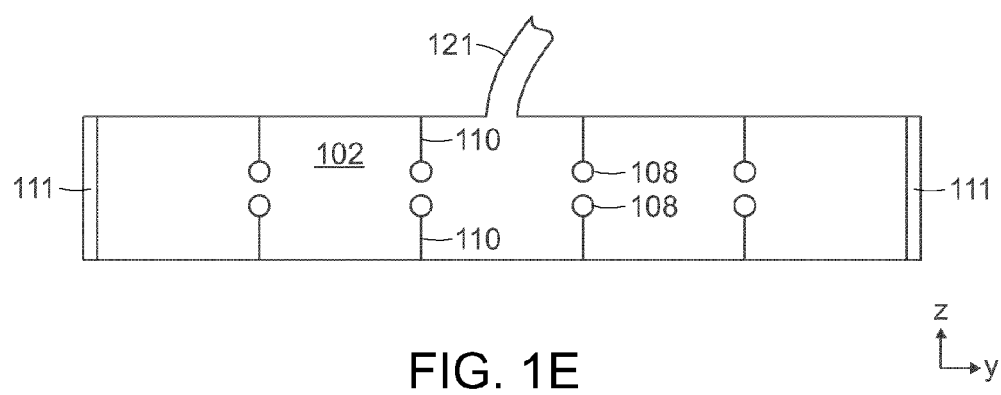
FIG. 1E is a cross-section view of filler material showing x-y stabilizers and z-stabilizers.

As shown in FIGS. 1D and 1E, for example, the filler material 102 includes a plurality of stabilizer elements 108 (shown in phantom) that enable the collapse of the filler material in certain directions, while inhibiting it in other directions. In this embodiment, the stabilizer elements 108 include a plurality of stabilizing ribs, flexures or rods, made from a suitably rigid or semi-rigid material, such as plastic. The ribbed structure is configured to preferentially collapse along a specific axis to facilitate proper closure of the wound. The internal stabilizer elements 108 in this embodiment form a cross-hatched pattern as seen in FIG. 1D, though it will be understood that other configurations can be utilized. The spacing between the elements in the "open" state can be in a range of 1-2 cm, for example. The stabilizer elements 108 can be provided at different depths within the filler material, as shown in the cross-section view of FIG. 1E, which helps inhibit collapse in the z-direction. In some embodiments, z-axis stabilizer elements 110 can be utilized to inhibit collapse in this direction. In FIG. 1E, the z-axis stabilizer elements 110 are projections that extend vertically from the ribs 108. In other embodiments, separate z-axis stabilizers, such as rods or rib structures, can be employed.

In certain embodiments, the device 100 can include a flexible covering comprising peripheral stabilizer element 111 that extends around the outer periphery of the filler material 102, as shown in FIG. 1E. The stabilizer element 111 can include a rib structure that reinforces the filler material 102 in order to prevent collapse in the z-direction, as well as to inhibit tilting of the filler material in the z-y and z-x planes. Thus, preferred embodiments of the filler material preferentially contract in at least a first direction relative to a second direction upon application of a negative pressure. Thus, for example, the width will contract at a faster rate relative to the length, while the height (depth of the wound) does not contract a substantial distance.

In some embodiments, the tissue grasping anchor elements 106 can be included on the peripheral stabilizer element 111, and project out from the periphery of the filler material 102. This can be as an alternative to, or in addition to, providing the anchor elements 106 on a separate mesh or film. The peripheral stabilizer element 111 is preferably configured to expand and contract as necessary with the expansion and contraction of the wound filler material 102. Thus, in a preferred embodiment, the stabilizer element 111 has sufficient flexibility to contract and expand in the x- and y-directions (i.e., around the periphery of the filler material 102), but has adequate rigidity along the z-direction (i.e. along the height of the filler) to inhibit collapse or tilting in this direction.

Figure 1F:
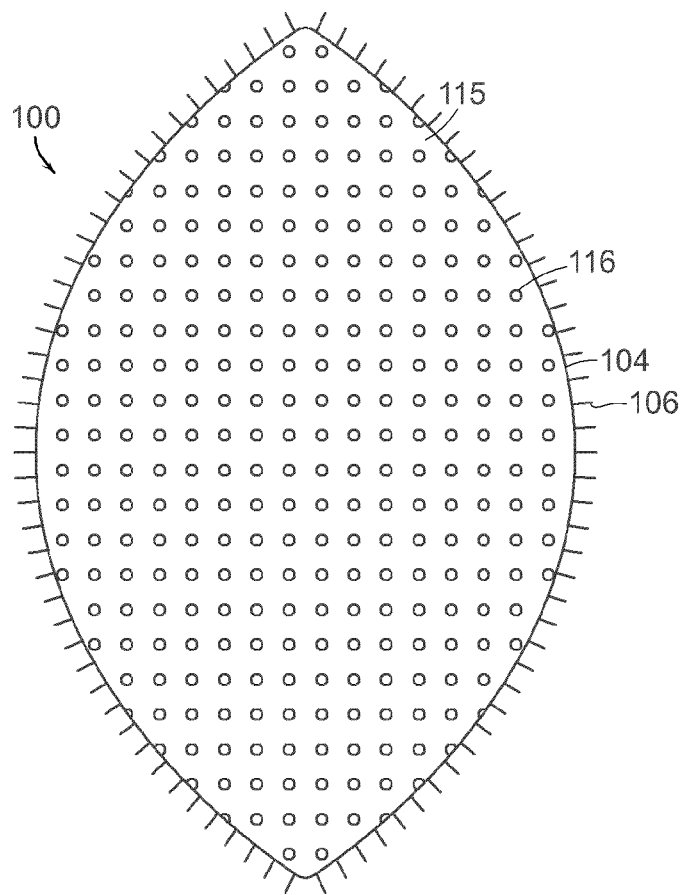
FIG. 1F is a bottom view of the wound closure device showing a smooth bottom surface and micropores for removing fluid from the wound site.
Figure 1G:
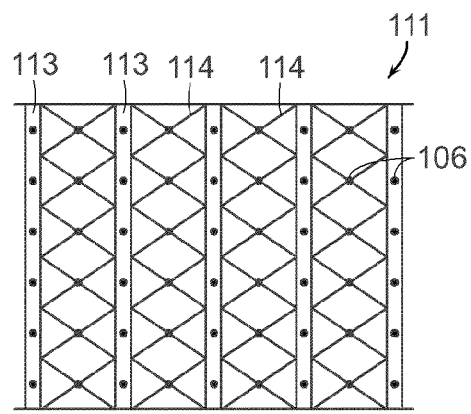
FIG. 1G is an elevation view of a peripheral stabilizer element.

An embodiment of a peripheral stabilizer element 111 is shown in elevation view in FIG. 1G. The stabilizer element 111 includes a plurality of stabilizing rods 113, oriented to inhibit collapse in the z-direction. The rods 113 are separated by a flexible material 114 that allows the stabilizer element 111 to expand and contract around the wound margin with the expansion and contraction of the underlying filler material. In this embodiment, the tissue anchor elements 106 are formed in the peripheral stabilizer element 111 and project out from the page.

Figure 2A:
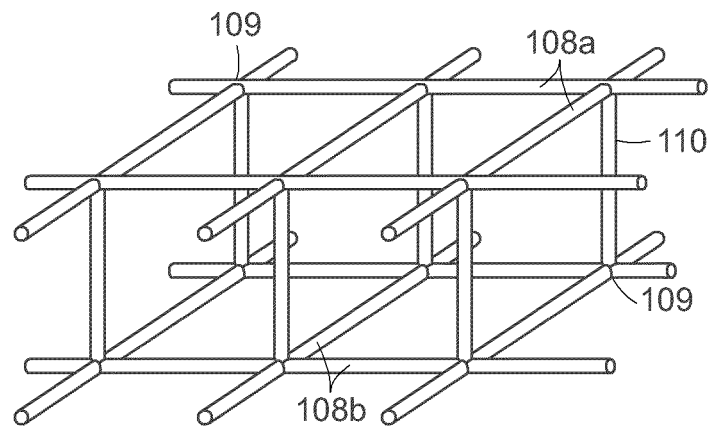
FIGS. 2A and 2B are perspective and side views, respectively, of a supporting endoskeleton.
Figure 2B:
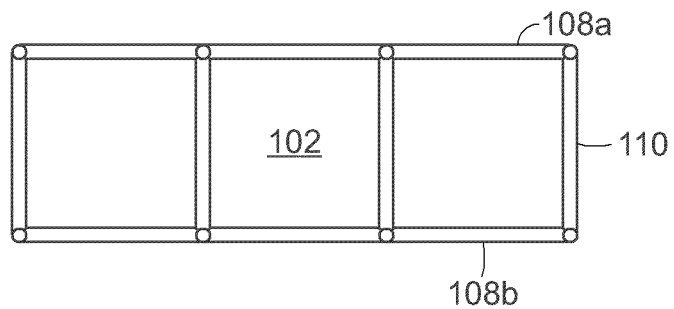

One embodiment of an endoskeleton for a wound filler material of the invention is shown in FIGS. 2A and 2B. The endoskeleton includes a first set of x-y stabilizer elements 108a and a second set of x-y stabilizer elements 108b that are connected by a plurality of z-axis stabilizer elements 110. During collapse of the filler material 102, the respective x-y stabilizer elements 108a, 108b are collapsible in the x-y directions, but the z-axis stabilizer elements 110 inhibit collapse in the z-direction. In preferred embodiments, the stabilizer elements can articulate with respect to one another during collapse. The joints 109 in the structure can be hinged or have a reduced thickness to accommodate the flexing of the system. The flexures between the joints may also flex to accommodate the desired compression along the first, or lateral, axis 117 (see FIG. 4B). Some expansion can occur along the second, or longitudinal, axis 119 as the device compresses. The frame material can have a shape memory characteristic, which in combination with the suction force, defines the force level applied to the tissue.

Figure 3A:
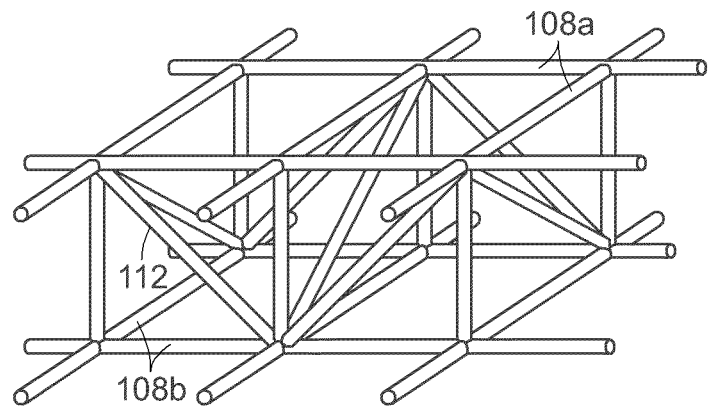
FIGS. 3A and 3B are perspective and side views, respectively, of a supporting endoskeleton with support trusses.
Figure 3B:
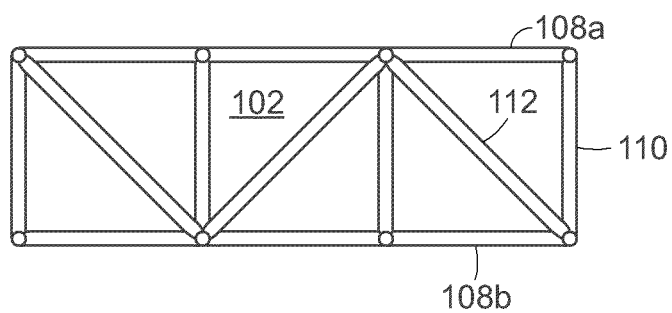
Figure 3C:
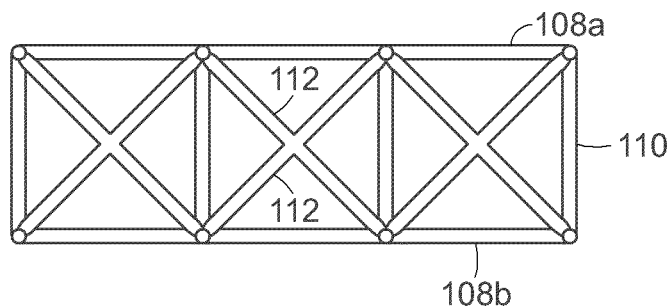
FIG. 3C is a side view of a supporting endoskeleton with x-shaped support trusses.

In another embodiment, shown in FIGS. 3A and 3B, the endoskeleton includes truss stabilizers 112 to inhibit tilting of the filler material 102 during collapse. The truss stabilizers 112 keep the upper 108a and lower 108b x-y stabilizers aligned with one another as the filler material 102 collapses. In some embodiments, the truss stabilizers 112 can be rigid in certain directions and relatively less rigid in other directions (for example, the truss stabilizer can be bowed) to promote collapse in certain directions. FIG. 3C illustrates an alternative embodiment having truss stabilizers 112 in an "x"-shaped pattern.

A preferred embodiment of the present invention employs an endoskeleton structure in which one or more of the stabilizer or flexure elements 108, 112 comprise hollow tubes or cavities 115. The hollow tube elements 108, 112 can be used to alter the elastic characteristics of the structure and thereby adjust the lateral displacement and force characteristics of structure. The diagonal flexures 112 extend between the planes formed by the lateral elements 108a and 108b.

The use of hollow tube elements in the elastic structure can also be used for the delivery of drainage fluid, medication, oxygen or other media into the wound. The tubes 108, 112 can contain media upon implant into the wound that is subsequently released into the wound or can be connected to an external source. The tube walls can have pores that open to accommodate fluid flow into the wound from within the tube elements or cavities therein. The location of tubular elements, as opposed to solid rods or flexures, can be selectively positioned within the structure depending on the preferred delivery location. For example, the flexures 108 along the lateral walls can be used for delivery to the regions being drawn together under negative pressure. Alternatively, the flexures in the bottom plane of the skeleton can be used for delivery to the underlying tissue structure or organs.

The stabilizing endoskeleton in certain embodiments can be made, in whole or in part, from a shape memory material. Various shape memory materials can be used which return from a deformed state (temporary shape) to their original (permanent) shape. This change in shape can be induced by an external stimulus or trigger. In one embodiment, the original or "permanent" shape of the endoskeleton is the "collapsed" configuration of the wound closure device, or the shape that will bring about wound reapproximation. When the wound closure device is initially inserted in the wound opening, the endoskeleton is in a deformed or temporary state and embedded within the filler material. The endoskeleton can preferentially revert to its original or "collapsed" state or, alternatively, cause the device to expand to engage the tissue. The "collapse" force of the shape memory endoskeleton can be in addition to or an alternative to the vacuum force induced by the negative pressure source. In certain embodiments, the application of a negative pressure to the wound closure device, which can cause the endoskeleton to revert to its original state.

FIG. 1F shows the bottom of the wound closure device 100 according to one embodiment. The device 100 in this embodiment includes a smooth bottom surface 115. This material can be biocompatible film to be used with, such as, provided in conjunction with the Renasys® system available from Smith & Nephew. A preferred embodiment can also be used with a gauge as also provided in the Renasys® system. The bottom surface 115 provides a low-friction interface between the wound closure device 100 and the underlying tissue. In the case of an abdominal wound, for example, the underlying tissue can include internal organs, such as the intestines. The smooth bottom surface 115 enables the filler material 102 to contract and expand freely without interference from the underlying tissue, and without damaging the underlying tissue. In a preferred embodiment, the bottom surface 115 includes micropores 116 (shown with size exaggerated in FIG. 1F for purposes of illustration) that allow the passage of fluid through the bottom surface 115 and into the device 100 for removal from the wound site. The wound closure device can also be inserted over a separate layer of material so that the device with contract on top of the sliding layer.

In some embodiments, the micropores 116 can have different sizes in different regions and/or can have different pore densities in different regions in order to direct different force levels of the vacuum source to different regions of the device 100. Similarly, the filler material 102 can be engineered with different internal pore sizes and/or pore densities to direct the distribution of forces from the vacuum source to different areas of the device 100.

Figure 4A:
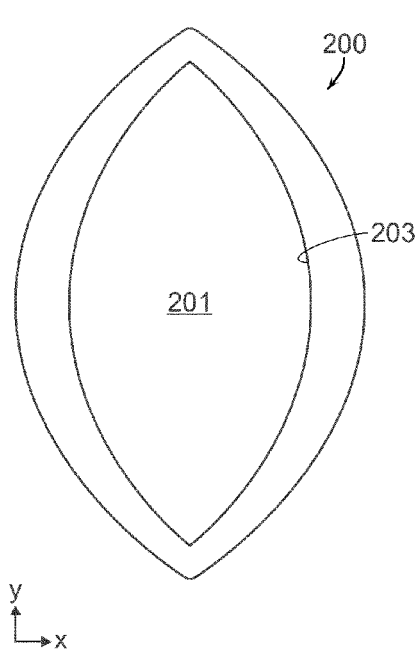
FIGS. 4A-C illustrate a wound closure device of the invention closing a wound.
Figure 4B:
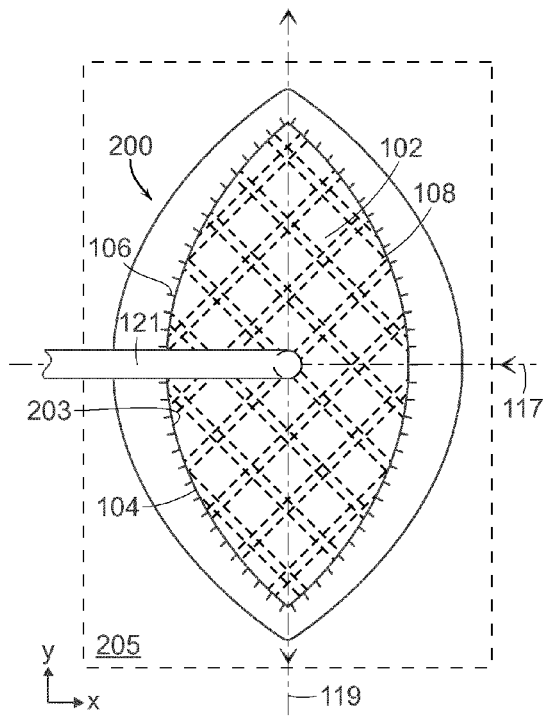
Figure 4C:
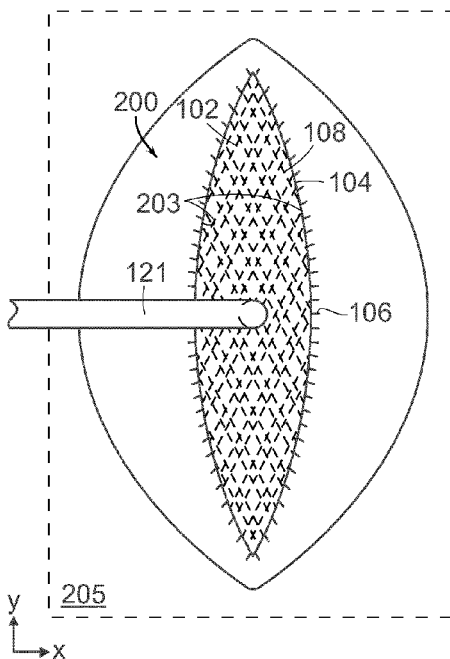

FIGS. 4A-4C illustrate the use of the present device 100 to close a wound 200. The wound 200 includes a wound opening 201 and a wound margin 203, as shown in FIG. 4A. In FIG. 4B, a wound closure device 100 is placed within the wound opening 201 so that the tissue grasping surface 104 is contacting the wound margin 203. In certain embodiments, the wound closure device 100 can be formed by trimming or tearing the filler material 102 to the proper size, and then attaching the tissue grasping elements 106 around the periphery of the filler material 102. In one embodiment, the grasping elements 106 are attached by attaching a two-sided barbed mesh to the filler material 102, where the outward-facing prongs are designed for grasping tissue and the inward-facing prongs are designed to secure the mesh to the filler material 102. A tube 121 connects the filler material 102 to the negative pressure source. The area of the wound 200, including the filler material 102, can be covered by a sealing drape 205.

In the embodiment of FIG. 4B, the filler material 102 includes a plurality of internal stabilizer elements 108 (shown in phantom) that provide the filler material 102 with a preferential collapse characteristic. The stabilizer elements 108 help control the collapse of the filler material 102, and the resulting displacement of the tissue around the wound margin 203, in the x- and y-directions. Additional stabilizer elements can be provided to control or inhibit collapse along the z-direction. As described above in connection with FIG. 1D, the stabilizer elements 108 in this embodiment include a cross-hatched configuration.

FIG. 4C illustrates the wound 200 following the application of a negative pressure to the wound closure device 100. The tissue anchor elements 106 grab the tissue margins 203 and cause displacement of the tissue margins 203 as the filler material 102 collapses. As seen in the FIG. 4C, the filler material 102 collapses in the x- and y-directions in such a manner as to reapproximate the tissue at the wound margin 203. In the embodiment of FIGS. 4B and 4C, the crosshatched configuration of the stabilizer elements 108 help control the direction of tissue displacement during collapse. The largest amount of tissue displacement in this embodiment is in the central region of the wound 200, where the opening 201 is widest, and this displacement is primarily inward along the x-direction. Away from the central region (e.g., at the top and bottom of the wound as shown in FIGS. 4A and 4B), where the wound margins are closer together, less displacement in the x-direction is needed to reapproximate the tissue.

Figure 4D:
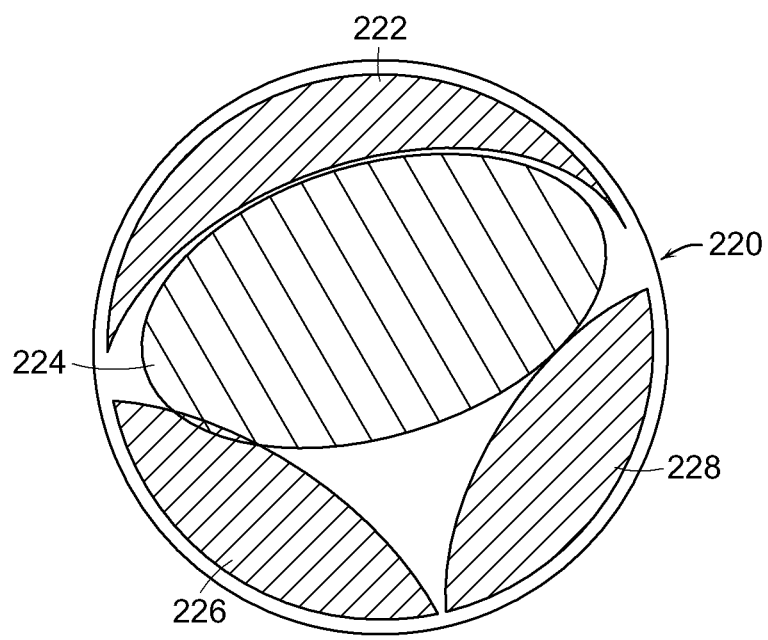
FIGS. 4D-4E illustrate the use of a plurality of wound closure elements used for wounds of different shapes.
Figure 4E:
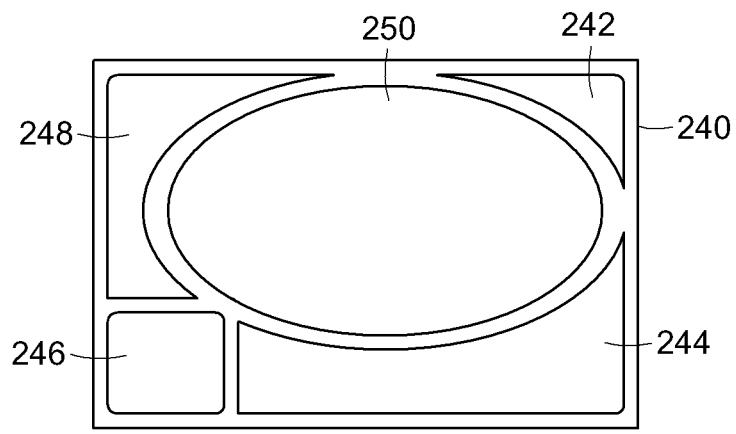

In general, the inward collapse of the filler material along the y-direction is undesirable. In fact, during tissue reapproximation, the wound 200 will tend to elongate in y-direction as the wound margins close in the x-direction. In preferred embodiments, the internal stabilizer elements 108 promote the collapse of the filler material in a manner that provides wound reapproximation. In the embodiment of FIG. 4-C, for example, during filler collapse the crosshatched stabilizer elements 108 straighten out relative to one another, similar to an accordion gate. The largest displacement is in the central region of the filler 102, along the x-direction. The stabilizers 102 generally inhibit inward collapse along the y-direction. As the stabilizers 108 straighten out, they can also facilitate elongation of the wound in the y-direction to allow proper tissue reapproximation. Shown in FIGS. 4D-4E are different shaped wounds 220, 240 in which a plurality of wound closure elements are used in combination to fill the wound. In FIG. 4D, elements 222, 224, 226 and 228 have different shapes that are cut or trimmed to size so as to substantially fill the wound that in this example, is circular in shape. When negative pressure is applied, the elements work together to close the wound in a desired direction. FIG. 4E illustrates a rectangular wound 240 using closure elements 242, 244, 246, 248 and 250 to fill the wound 240. The tissue anchors of each closure element can also attach to the adjoining closure element(s). With suction applied to the central elements 224, 250, the adjoining elements are drawn towards the central elements to close the wound.

The wound closure device 200 can remain in this configuration for a period of several days or weeks to facilitate closing and healing of the wound 200. After a period of healing, the device 100 can be removed and optionally replaced with a smaller device. After the wound has been sufficiently closed using the present device, it can be stitched closed.

Figure 5:
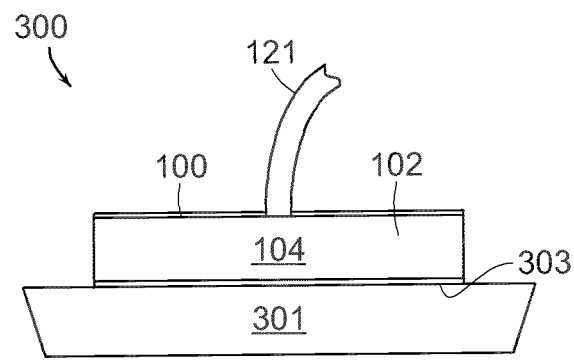
FIG. 5 illustrates a two-stage negative pressure wound treatment and negative pressure wound closure (NPWT/NPWC) device.

FIG. 5 illustrates a two-stage negative pressure wound treatment and negative pressure wound closure (NPWT/NPWC) device 300. The device includes a negative pressure drainage/fluid management component 301, as is known in the art, that connects with an overlying negative pressure wound closure device 100. The wound closure device 100 includes a collapsible wound filler material 102 and a tissue grasping surface 104, substantially as described above. A tube 121 connects the device 300 to a single pump for applying a negative pressure to the wound closure and wound treatment components. The device 300 can include interchangeable parts depending on the need of a specific wound application. In one embodiment, the device 300 is used for abdominal wounds in one example, and can also be used for mediastinum and fasciotomy wounds.

In a preferred embodiment, the filler material 102 is able to "slide" within the total NPWT/NPWC device 300. The filler material 102 includes a sliding surface 303 at the interface between the wound closure and fluid management components. The sliding surface can comprise a treated surface or a separate layer of material. The sliding surface 303 facilitates the free contraction of the wound closure component, without interference from the fluid management component. The underlying fluid management component 301 can be specifically configured to manage fluid only and to not generate granulation, as this can slow down or inhibit the "slide."

Figure 6:
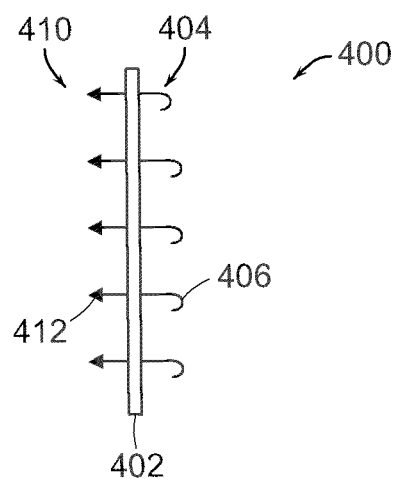
FIG. 6 illustrates an enlarged view of a preferred embodiment of the tissue anchor system in accordance with the invention.

FIG. 6 illustrates an enlarged view of a preferred embodiment of the tissue anchor system 400 in accordance with the invention. One side of the material 402 has a first group of anchor elements 404 that are adapted to grasp the filler material. The first anchor elements 404 can be shaped to grasp the filler material such as with a distal hooked shape 406. As material 402 must attach to the filter with a certain grasping strength in order to apply a sufficient pulling force on the tissue, a specified force level F, must be applied to remove the hooks from the filler material that exceeds the pulling force being applied to the tissue. Similarly, as the tissue to be grasped by the material 402 has different structural characteristics then the filler material, a second group of anchor elements 410 adapted to grasp tissue can have a different shape and grasping force then the first anchor elements. In this embodiment, barbs 412 can have bilateral prongs 414 that tend to collapse upon insertion in tissue and yet expand when pulled in an opposite direction such that a certain pulling force can be applied to tissue. However, the prongs or cone shape anchor element has a release force such that the barbs can be manually pulled from the tissue without causing injury.

Figure 7:
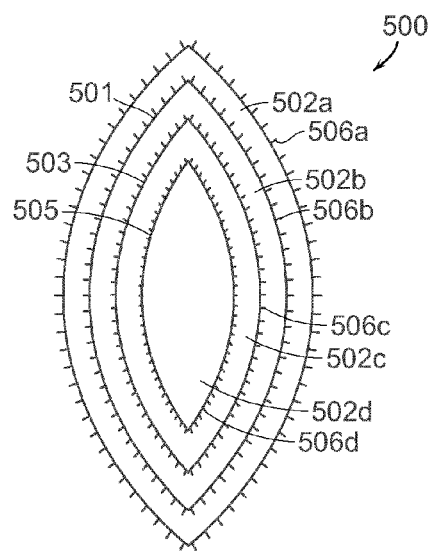
FIG. 7 illustrates an embodiment of a wound filler material having a tear-away or cut-away design for accommodating different wound sizes, with tissue anchors embedded within the filler material at pre-determined cleavage points.

FIG. 7 illustrates an embodiment of a wound filler material 500 having a tear-away or cut-away design for accommodating different wound sizes. The filler material 500 includes natural cleavage lines 501, 503, 505 that allow the size of the material to be adjusted to fit the wound to be closed. The material 500 is designed to be torn or cut at the cleavage lines to remove one or more portions 502a, 502b, 502c of the material and adjust the size of the material. Sets of tissue anchors 506a, 506b, 506c, 506d are embedded within the filler material at pre-determined cleavage points, and become exposed as the respective outer portions 502a, 502b, 502c are removed. The tissue anchors 506a, 506b, 506c, 506d can be associated with a stabilizing endoskeleton structure, such as described above in connection with FIGS. 1-4. In some embodiments, the stabilizing endoskeleton structure can include pre-defined cleavage or attachment points to remove portions of the stabilizer structure as the size of the filler material 500 is adjusted.

Figures 8A, 8B:
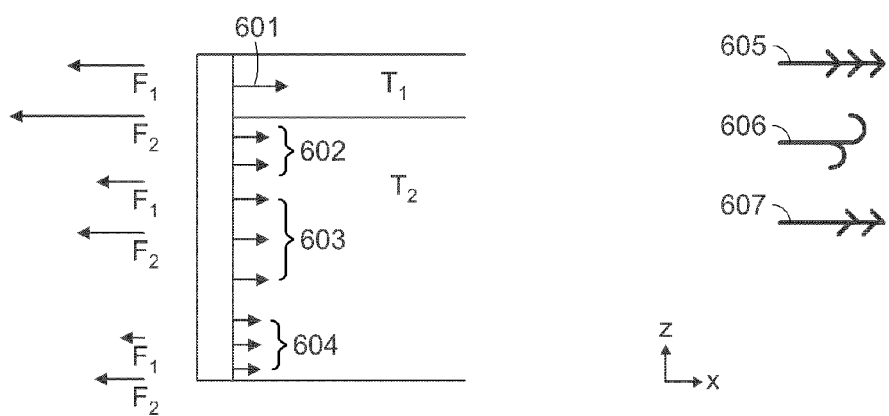
FIG. 8A is a side view of a tissue grasping surface, illustrating different tissue anchors for different types of tissue ($T_1$, $T_2$) and the respective force profiles for the anchors, including the maximum force applied during vacuum closure ($F_1$) and the force required to remove the anchors from the tissue ($F_2$) without damaging the tissue.
FIG. 8B illustrates different designs for a tissue anchor of the invention.

FIG. 8A is a side view of a tissue grasping surface, illustrating different tissue anchors 601, 602, 603, 604 for different types of tissue ($T_1$, $T_2$). Also illustrated is an example of the respective force profiles for the anchors, including the maximum force applied to the tissue during vacuum closure ($F_1$) and the force required to remove the anchors from the tissue ($F_2$) without damaging the tissue. In one embodiment, the characteristics of the tissue anchors vary to provide different force profiles across the interface between the wound closure device and the surrounding tissue. For example, for the upper tissue layer(s), $T_1$, the anchor 601 is designed to attach to collagen material, such as in the dermis. The anchor 601 has a different force profile ($F_1$ and $F_2$) on the upper tissue layer(s), $T_1$, as shown in FIG. 8A. At the lower tissue layers $T_2$, the anchors 602, 603, 604 are designed to attach to fatty tissue of subcutaneous layer. Generally, a smaller force profile is needed to secure the anchors to this tissue.

Figure 8C:
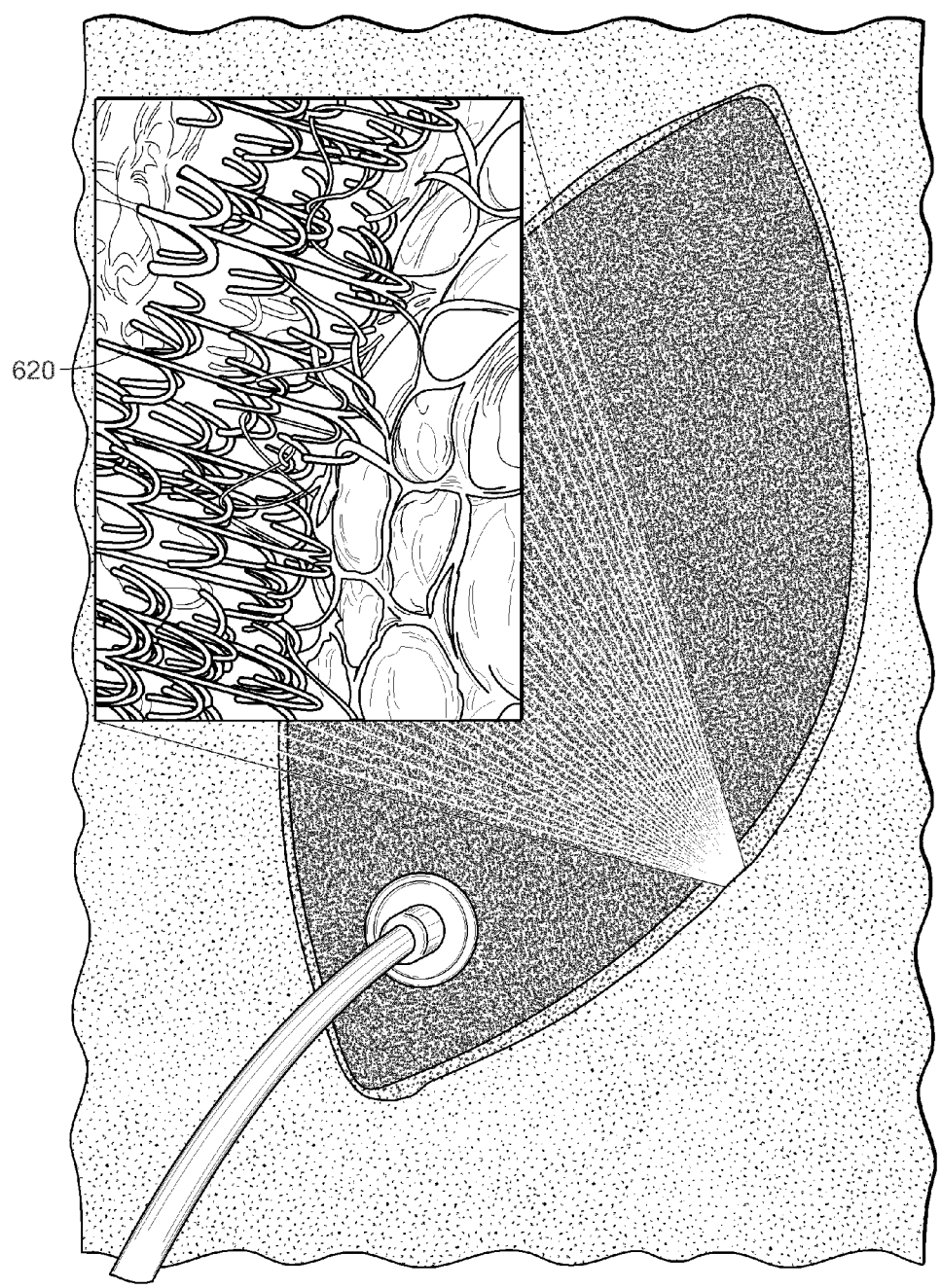
FIG. 8C illustrates an enlarged view of tissue anchor elements on the peripheral surface of an oval shaped wound closure device.

The characteristics of the anchors, and their resulting force profiles, can vary by a number of parameters, such as the length of the anchor, the shape of the anchor, the structure of grasping features, the material(s) used for the anchor, the relative flexibility/rigidity of the anchors, and the spacing/ density of the anchors. In FIG. 8A for example, anchor 601 is significantly longer than anchors 602, 603, which in turn are longer than anchors 604. FIG. 8A also illustrates varying the density of anchors, such as shown in 602, 603 and 604. FIG. 8B illustrates three examples of different types of grasping features, including a barbed configuration 605, a staggered hook configuration 606, and a staggered barbed configuration 607. Other suitable grasping features can be utilized such as the anchor elements 620 shown in the enlarged perspective view of FIG. 8C. The anchoring process can be augmented by suturing the filler material or supporting endoskeleton to the tissue. The force profile can also be varied by controlling the vacuum force distribution in the filler material, such as by varying the pore size and/or pore density of the filler.

The wound closure device of the invention can be provided in kits for closing different types of wounds (e.g., abdominal, fasciotomy, etc.). The tissue grasping surface can be optimized for different types of tissue such as collagen, fatty tissue and muscle, depending on the structure of the tissue at the wound site.

Figure 9A:
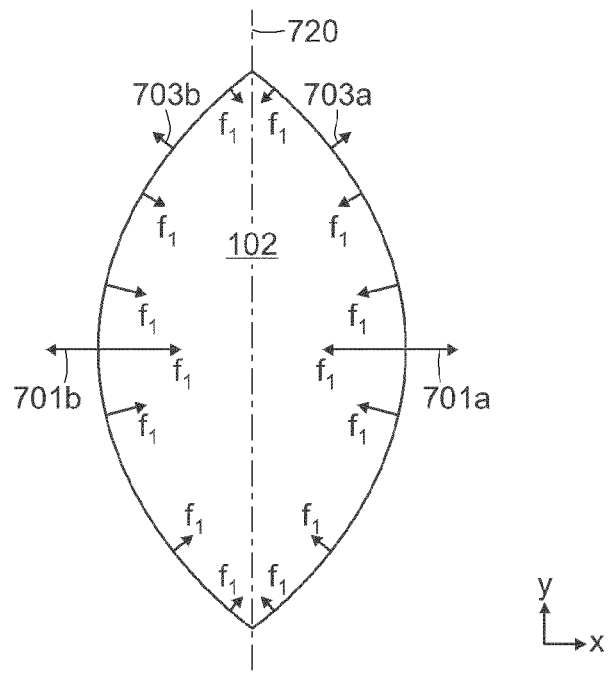
FIG. 9A is a schematic illustration of a wound closure device positioned within a wound showing the different force profile around the margin of the wound according to one embodiment.
Figure 9B:
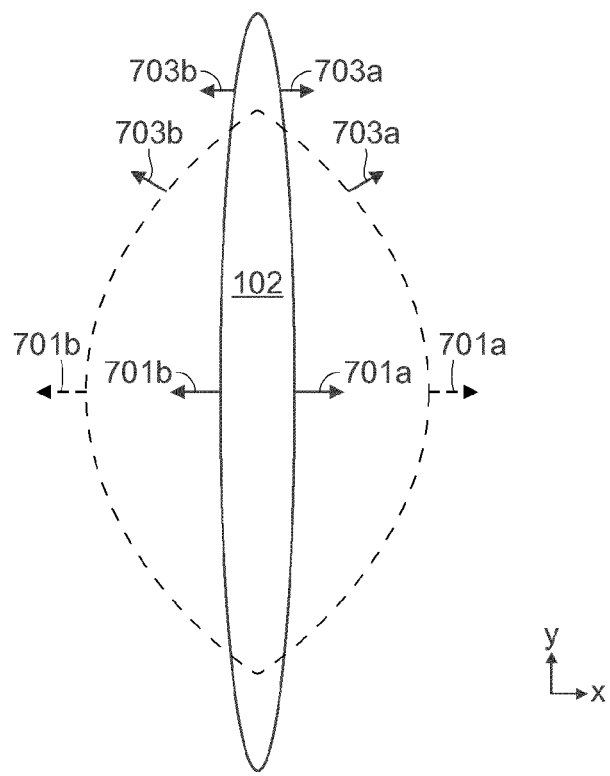
FIG. 9B illustrates the wound closure device of FIG. 9A after a period of wound closure and healing, with the original configuration of the wound and wound closure device indicated in phantom.

In certain embodiments, the force profile of the wound closure device is variable around the periphery of the wound. An exemplary embodiment is illustrated in FIG. 9A, which shows the force profile ($f_1$) exerted on the wound margins at a plurality of locations on the periphery of the wound. In this embodiment, the largest $f_1$ is at the central region of the wound filler 102, where the wound opening is widest and the wound closure force is entirely or nearly entirely in the x-direction. Moving towards the top and bottom regions of the wound, the closure force ($f_1$) is much smaller. One reason for this is because the wound opening is much smaller in these regions, and a much smaller force is needed to reapproximate the tissue. Also, the inward force exerted in these regions includes components in both the x- and y-directions. Thus, a smaller force profile is preferable to avoid the inward collapse of the tissue in the y-direction. As illustrated in FIG. 9B, as the wound closes and heals from an initial state (indicated by dotted lines) to a later state (indicated by solid lines), it becomes elongated in the y-direction. Thus, the displacement of tissue anchors 701a and 701b is exclusively in the x-direction and in the direction of the closure force ($f_1$), while the displacement of tissue anchors 703a, 703b is both inwards in the x-direction (in the direction of the closure force) and outwards in the y-direction (opposite the direction of the closure force). Thus, a smaller $f_1$ is preferable in these regions to provide more "play" between the anchor elements and the surrounding tissue. Alternatively, the wound closure device is configured so that it does not elongate, but rather does not change its length along the long axis 720.

The variation in the force profile around the periphery of the wound closure device can be achieved in a variety of ways, such as varying the spacing/density of the tissue anchors, the types of anchors, length of anchors, or configuration thereof, etc. For example, in FIGS. 9A and 9B, anchors 701a, 701b are longer and penetrate deeper into the tissue compared to anchors 703a, 703b. The force profile can also be varied by controlling the vacuum force distribution in the filler material, such as by varying the pore size and/or pore density of the filler.

On one embodiment, a method of fabricating a wound closure device of the invention includes forming a stabilizing endoskeleton of rigid or semi-rigid material and forming a collapsible filler material over the endoskeleton. The stabilizing endoskeleton can be formed using a molding process, and can be molded as an integral unit or in one or more components that are then assembled to form the endoskeleton. Different components of the endoskeleton can have different thicknesses and/or degrees of rigidity to provide varying levels of rigidity and flexibility along different directions. The endoskeleton can be assembled by joining components, such as by using a suitable adhesive or other joining process such as by inserting rods into tubular segments. In certain embodiments, at least some of the components can be assembled to provide articulating joints. In preferred embodiments, the filler material is formed by mixing together appropriate metered amounts of constituent substances, (e.g., isocyanates, polyols, catalysts, surfactants, blowing agents and the like in the case of polyurethane foam), dispensing the reacting mixture into a mold, and then curing and demolding the material. Optionally, the material can then be cut or trimmed to the finished shape. In preferred embodiments, the endoskeleton support structure is assembled and placed into the mold, and the filler material is molded around the endoskeleton. An example of a biodegradable foam product suitable for the present wound closure device, and methods of fabricating such a foam, is described in U.S. Published Application No. 2009/0093550 to Rolfes et al., the entire contents of which are incorporated herein by reference.

Figure 10A:
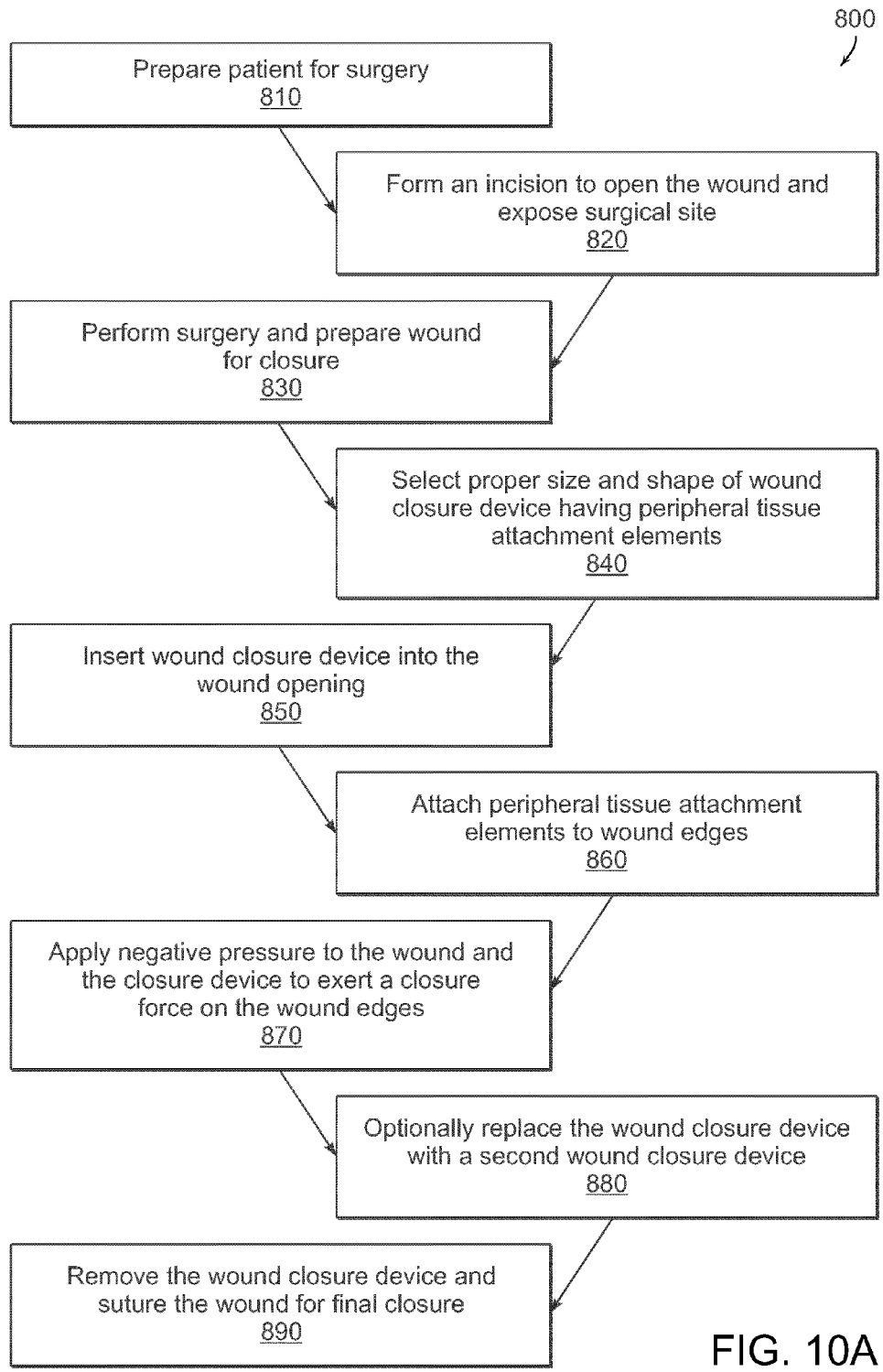
FIGS. 10A and 10B schematically illustrate processes of using a wound closure device in accordance with preferred embodiments of the invention.

A method of performing a surgical procedure 800 using a wound closure device in accordance with preferred embodiments of the invention as illustrated in FIG. 10A. After preparation 800 of the patient for surgery, an incision is made 820 to expose the surgical site, typically in the abdomen. After the procedure is performed, the wound is prepared 830 for closure. The proper size and shape of the wound closure device is selected 840 with the peripheral tissue attachment members positioned around the circumference or outer wall surface of the device. The device is inserted 850 into the wound and the tissue attachment elements are inserted 860 into the tissue. Negative pressure is then applied 870 to exert a closure force on the wound edges. Depending on the particular application, large wounds may require placement 880 of a smaller second closure after removal of the first larger device. Finally, the device is removed 890 and the wound is closed, typically by suturing.

Figure 10B:
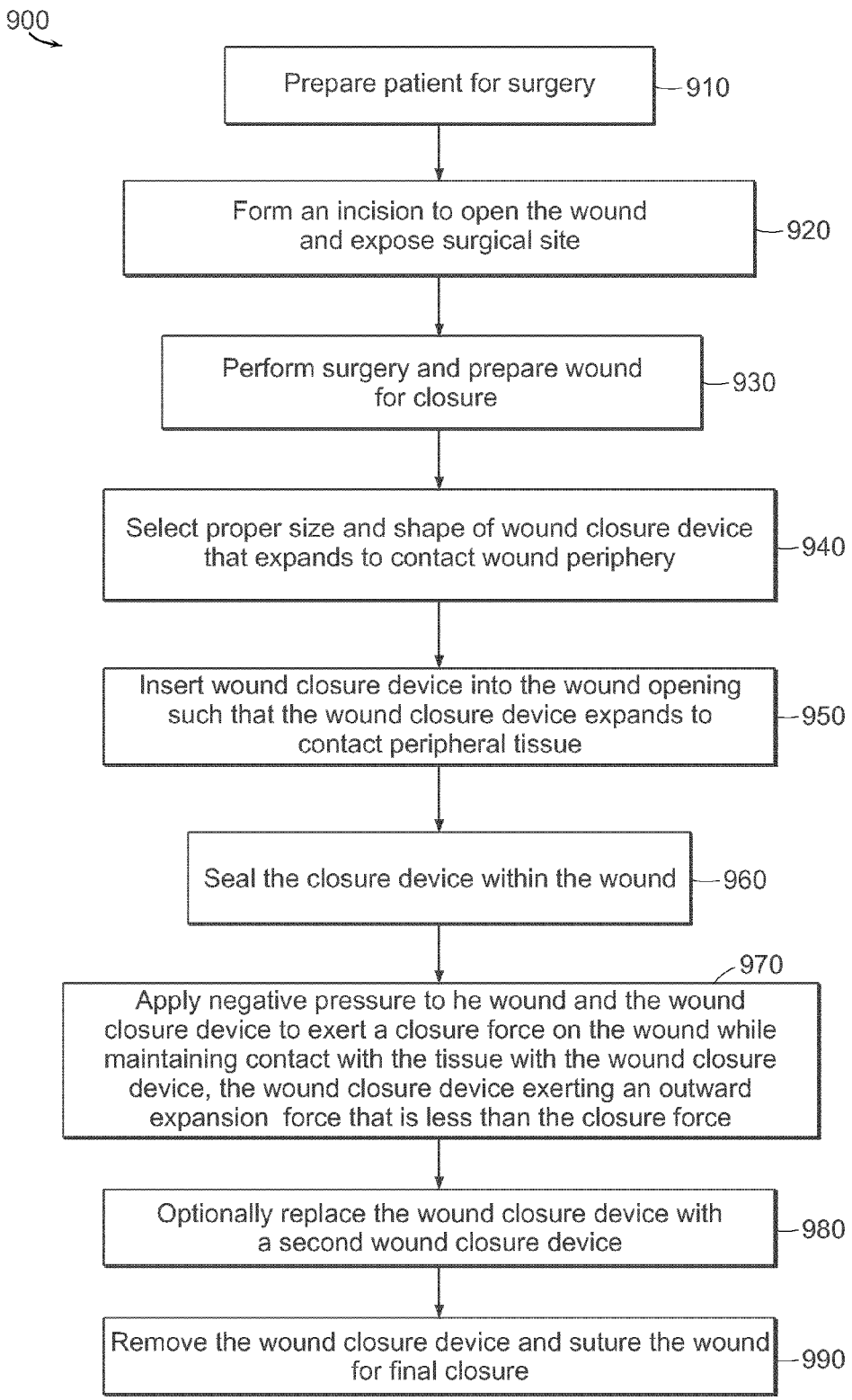

In a preferred embodiment in which tissue anchors are not used, a method 900 for wound closure is described in connection with FIG. 10B. In this embodiment the patient is prepared for surgery 910, an incision or other means are used to open or expose 920 the wound and the procedure is performed 930. The wound closure device suited for the shape of the wound is selected 940 and inserted 950 into the wound. In this embodiment, the wound closure device flexes or expands under its inherent expansion characteristics to contact the wound margins. The wound is then sealed 960 and negative pressure is applied 970. Sufficient negative pressure is applied so that the expansion force exerted by the device on the wound margin is less than the closure force applied to the wound and the device such that the wound closes at a controlled rate. This provides a procedure in which the device maintains contact with the wound margin and thereby reduces the occurrence of typing of the device within the wound during closure. As in prior embodiments, the device can be replaced 980 as needed prior to wound closure 990, however, the need for replacement is reduced by preventing the formation of gaps between the wound margins and the device.

Certain types of wounds that can be treated with negative pressure wound therapy involve the separation by incision of subcutaneous tissue to form a wound opening. This procedure is frequently used to access underlying structures, organs or injuries. The lateral displacement of subcutaneous tissue can contribute additional difficulties for the treatment of the resulting wound.

Illustrated in FIG. 11A is a wound incision 900 in which tissue region 906,908 have been separated to access an underlying tissue region 902 for treatment. The lateral displacement of regions 906, 908 from their respective positions overlying region 902 has caused further separation between the displaced regions 906, 908 and the underlying structure. In the case of an open abdominal wound, the underlying structure can be the large and small intestines, which can be subject to infection and/or elevated fluid pressure.

Additionally, there can be separation between the fascia 909, 911 and abdominal muscle and the overlying subcutaneous tissue 906, 908. Consequently in FIG. 11A, the system can optionally include three components, the pad 907 positioned between the abdominal cavity 902 and the fascia that can be used to permit sliding movement and utilize negative pressure, secondly, a seroma pad 925, described in greater detail hereinafter, positioned between the fascia and overlying tissue and, thirdly, the wound closure element 918. The negative pressure region 918 can be in fluid communication with the underlying layer 925, which extends laterally to sections 914 and 915 which are situated between overlying tissue 906, 908, respectively, and the underlying abdominal muscle and fascia structure 911, 909. One or both sides of the sections 914, 916 can have tissue anchors 926, 928 as described previously. Dotted line 921 indicates a region through which negative pressure is applied to all three layers.

After insertion of layer 925, the compressible wound closure element 918 is inserted followed by sealing drape 905 and the closer device 940 and fluid control tube 942. The pad 907 operates to drain fluid 910 from the abdominal cavity by negative pressure through elements 925 and 918.

In the case where adjoining tissues need treatment utilizing negative pressure or require stabilization such as by pad 925, a wound treatment system can be used in combination with the systems and methods described herein. Shown in FIG. 11B is a top view of a system utilizing a negative pressure closure system 918 as described generally herein and a seroma pad or tissue adhesion element 925. The shape of pad 925 can also be circular and be without apertures or tissue anchors, for example. The number of drains can be in a range of 6-10 that extend in a radial direction with uniform angular spacing between the drain elements.

Thus a preferred embodiment of the present invention provides a pad or surgical drain device 925 for the prevention and treatment of seromas as well as for general use in promoting drainage of surgical wounds and wound closure. The drain device can include a plurality of drain tubes 935 disposed on a substrate termed an "adhesion matrix," which is designed to promote tissue adhesion within the seroma or wound space. The adhesion matrix has a conformable configuration and is made of a compliant material having planar surfaces that can bend to adapt to the shape of the wound space.

In a preferred embodiment, the adhesion matrix contains a plurality of apertures 927, or gaps in the matrix material, which allow tissue contact across the matrix, so as to promote adhesion and wound closure. Thus, a tissue surface on a first side of the matrix can directly contact a tissue surface on a second, or opposite, side of the matrix to promote rapid healing and stabilization of the wound. The number, size and distribution of the apertures 927 extending through the matrix can be selected based on the geometry of the wound. For abdominal wounds, for example, the drain tubes can be positioned in a fan shaped array with a plurality of three or more tubes extending from a manifold. The matrix and/or the tubing can be cut or shaped by the user to conform to the shape of the wound. The matrix can also be used as a medication carrier to assist in the administration of a drug to a patient. The matrix can optionally include a layer of adhesive on at least a portion of any of its surfaces. The drain tubes can be removed from the device once drainage flow is sufficiently reduced, and the adhesion matrix can remain within the body, where it is degraded and absorbed over time, remaining in place to optimize tissue healing. The matrix can comprise a porous biodegradable polymer material. As the plurality of tubes extend from a single exit site into the wound with spaced apart distal ends, a user can readily remove all the tubes simultaneously from the wound.

Figure 11C:
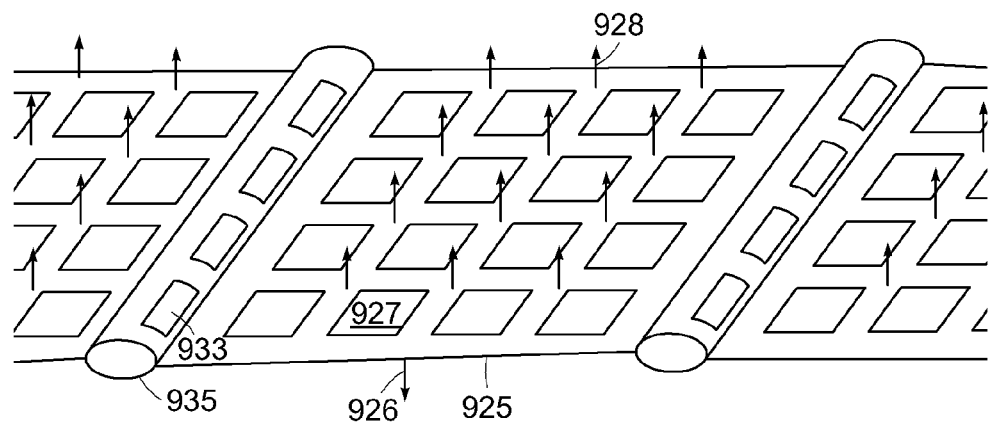
FIG. 11C shows a detailed perspective of a surgical drainage system in accordance with a preferred embodiment of the invention.

As shown in more detail in FIG. 11C, the surgical drain device 925 can include a tissue anchoring system, whereby the device is mechanically attached to surrounding tissues by an array of surface barbs or hooks 926, 928. These surface structures can be located on any exposed surface of the adhesion matrix. When the device is implanted, the surrounding tissues can be pressed against the barbs or hooks to embed them within the tissue and anchor the device. The use of surface barbs or hooks can be used in combination with a surgical adhesive, providing a much stronger bond between tissue layers than the adhesive alone, and providing temporary adhesion while the adhesive sets. The structure of the hooks can have various forms depending on the tissue they are intended to bind. Longer hooks can be used for loosely bound tissues such as fat or connective tissue, while shorter hooks can be used for denser tissues such as muscle. Anchors with more rigid stems can be utilized to penetrate denser tissues.

Another aspect of the invention is a system for surgical wound drainage. The system includes the drain device coupled to a wound closure device 918 as described generally herein together with a vacuum source, such as a pump, and a tube connecting the vacuum source to the drain tubes of the drain device. The system optionally also can include a fluid trap to collect drained fluid and a control unit to monitor and control the application of vacuum and the collection of fluid. Further components of the system can include a vacuum or pressure gauge, a flow meter, and a computer to monitor vacuum and flow and to regulate vacuum or flow. The pressure measurement can be used to control the level of applied pressure using a feedback control circuit. The wound closure device 918 can include the endoskeleton structure as described herein having external ribs extending from the outer surface and flexure arms or beams that have an intrinsic restoring force that varies as a function of position of each flexure element. The different flexure elements can have different restoring force depending upon their position within the structure as shown in FIGS. 2A-3C, for example. The endoskeleton accommodates expansion to fill the wound cavity and will collapse in a well-defined manner in response to the collapse of the wound under negative pressure. As described herein, foam or other filler material can be used within the flexure system. The endoskeleton can have a multilayered structure with the different layers collapsing along individual planes of the three dimensional structure within the wound without tilting of the structure.

Another aspect of the invention is a method for treating or preventing a seroma, or promoting the drainage or closure of a surgical wound. The method includes positioning the drain device described above into a seroma, or a surgical wound, such as a wound at risk of forming a seroma, and allowing the device to drain fluid from the wound for a period of time. The device can include surgical adhesive and/or barbs or hooks on its surface to create adhesion between tissue layers within the wound and to anchor the device in place. Drainage can be by gravity flow or can be vacuum assisted by attaching a vacuum source to the drain tubes of the device, using a manifold to merge the flow paths of the drain tubes to a common drain tube for collection. Negative pressure applied to the drain tubes can be used to hold the tissue layers above and below the device together until a surgical adhesive has set, or until the wound healing process binds the tissues together. The application of negative pressure further facilitates contact between tissue on opposite sides of the matrix through the apertures in the matrix to promote tissue adhesion. This improves the rate of healing while at the same time providing for drainage. Optionally, the drain tubes of the device have apertures 933 extending along their length and can be removed from the body after drainage flow is reduced, thereby reducing the burden for resorption by the body. Removal of the drain tubes can be facilitated by the inclusion of drain tube channels, or drain tube release tabs, within the adhesion matrix. Release of the drain tubes is then accomplished by sliding the tubes out of the channels or appropriately maneuvering the drain tube assembly to break release tabs. The adhesion matrix is allowed to remain in the seroma or surgical wound where it is resorbed over time.

The flow rate from the drain tubes can be regulated by flow control elements. The flow rate can also be measured or the pressure of fluids can be measured by ultrasound devices or by other methods. The system can also be used in conjunction with wound dressings that can also be attached to a negative pressure source to remove fluids from the wound.

Figure 12:
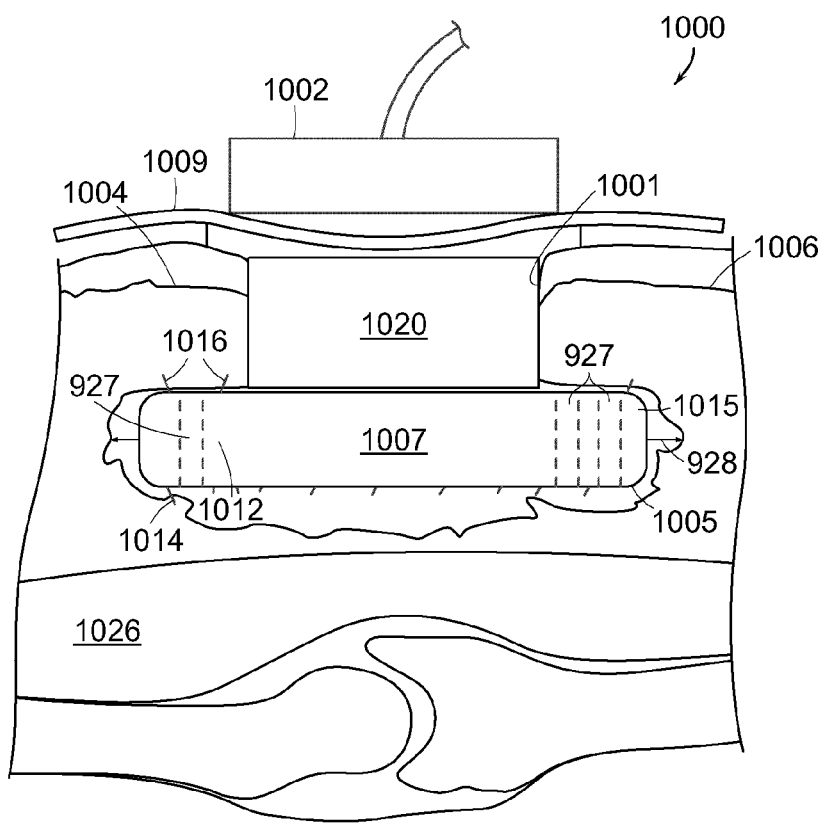
FIG. 12 illustrates a cross-sectional view of wound drain and closure system used for a surgically treated pressure ulcer in accordance with a preferred embodiment of the invention.

A preferred embodiment of the of the invention includes a negative pressure wound closure device 1000 for the treatment of surgically repaired ulcers as shown in FIG. 12. This type of wound often is characterized by a narrower wound opening 1001 that can have a generally circular or oval shape. The surgeon can use this opening to access tissue that must be removed to form a cavity 1005 that extends laterally. A first wound closure element 1007 extends laterally to regions 1012, 1015 which can include tissue anchors 1014, 1016 that serve to attach regions 1012, 1015 to tissue flaps 1004, 1006 above the regions 1012, 1015, respectively, as well as the underlying tissue 1026. The anchors 928 can also extend in a lateral direction. The second wound closure element 1020, as described previously, is in fluid communication with adhesion elements 1007, and enables the application of negative pressure to the channels 935 of regions 1012, 1015 that can be employed in the embodiment of FIG. 12. The closure element can include apertures 927 that allow for tissue contact through regions 1012 and 1015 as these elements compress under negative pressure.

Figure 13:
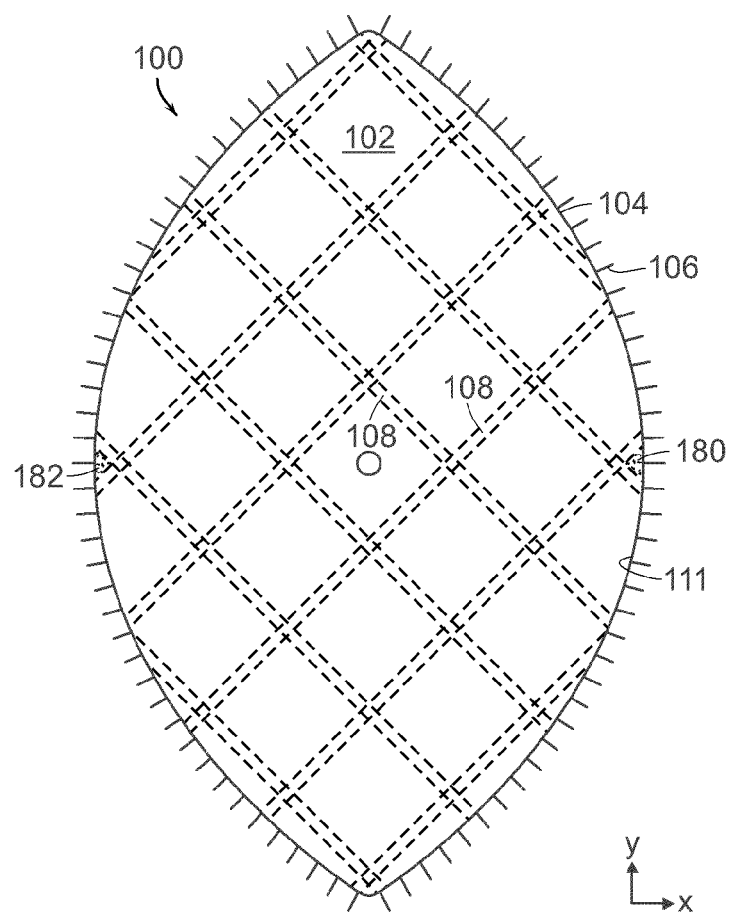
FIG. 13 illustrates a sensor system for measuring the wound closure force for a negative pressure wound closure system.

Illustrated in FIG. 13 is a sensor system 180, 182 for measuring wound closure force that can be exerted on the side walls of the tissue being drawn together. The sensor elements 180, 182 can be mounted to the internal flexible frame 108 or endoskeleton of the system and measure the amount of force exerted laterally on the tissue. For example, as the level of negative pressure applied to wound closure element 100 is increased, the sensors measure the increased force exerted on the tissue by anchors 106. Additional sensor elements can be mounted on the sidewalls of device 100, to measure the force distribution across the sidewalls. The flexure elements 108 can have a selected resiliency to enable controlled collapse of the device 100.

Figure 14:
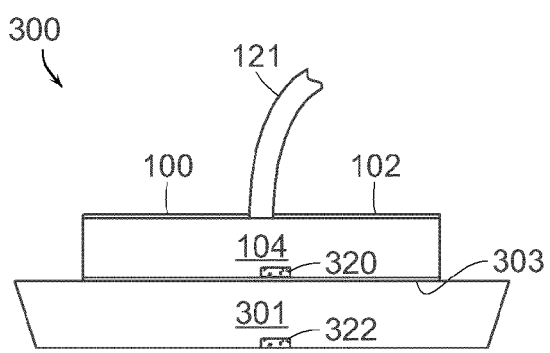
FIG. 14 illustrates a pressure sensor system for measuring wound pressure in accordance with preferred embodiments of the invention.

Shown in FIG. 14 is a pressure sensor system positioned to measure the pressure on underlying tissue. The sensor elements 320, 322 can measure pressure at the sliding interface 303 or at the bottom of panel 301, which can measure the amount of negative pressure at the tissue interface such as in the abdominal cavity. This can be used to monitor downward pressure on the abdominal cavity that can arise during compression of structure 104.

Figure 15:
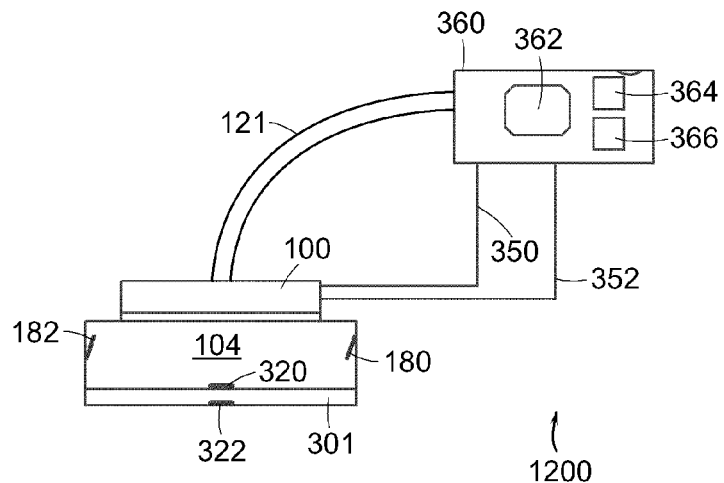
FIG. 15 illustrates a negative pressure wound closure system having a controlled pressure system.

The systems in FIG. 13 and FIG. 14 can optionally include a feedback control system 1200 that controls a level and/or distribution of negative pressure within the system. Such a feedback system 1200 is shown in connection with FIG. 15. Sensors 180, 182 can be connected to processor housing 360 using cable 350 and pressure sensors 320 and/or 322 can measure fluid pressure such that sensor data are transmitted to processor housing 360 using cable 352. A data processor 366 can be programmed to adjust the applied pressure via tube 121 to prevent injury to the patient and optimize the rate of wound healing. Data can be displayed on display 362 and a control panel 364 provides a user interface for operation of the system.

Figure 16A:
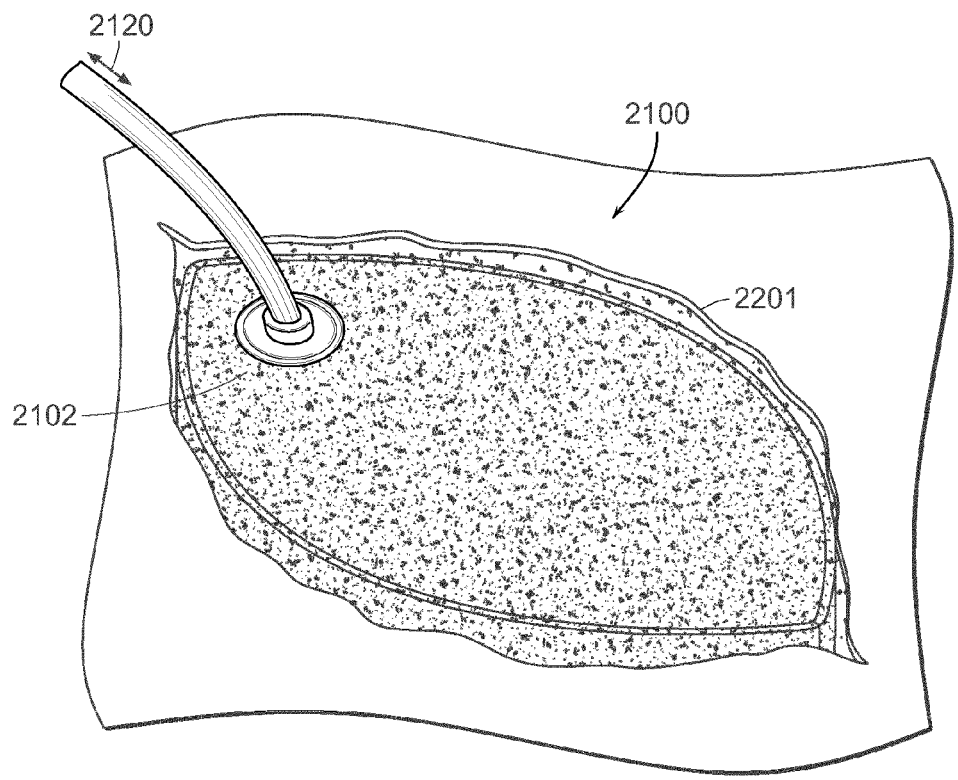
FIGS. 16A and 16B illustrate perspective and exploded views of a preferred embodiment of the device.

FIG. 16A illustrates a further exemplary embodiments of a wound closure device 2100 of the present invention. The device 2100 includes a wound filler material 2102 that is sized and shaped to fit within a wound opening 2201 of a human or animal patient. The device 2100 is further associated with a negative pressure source 2120, such as described with respect to FIGS. 1A-1F, which may be coupled to the filler material 2102, e.g., by a suitable coupling or conduit. As noted above, negative pressure source 2120 can be activated to apply a negative pressure to the filler material 2102. In general, the negative pressure causes a resulting pressure differential which causes the device 2100 to contract or "collapse."

Figure 16B:
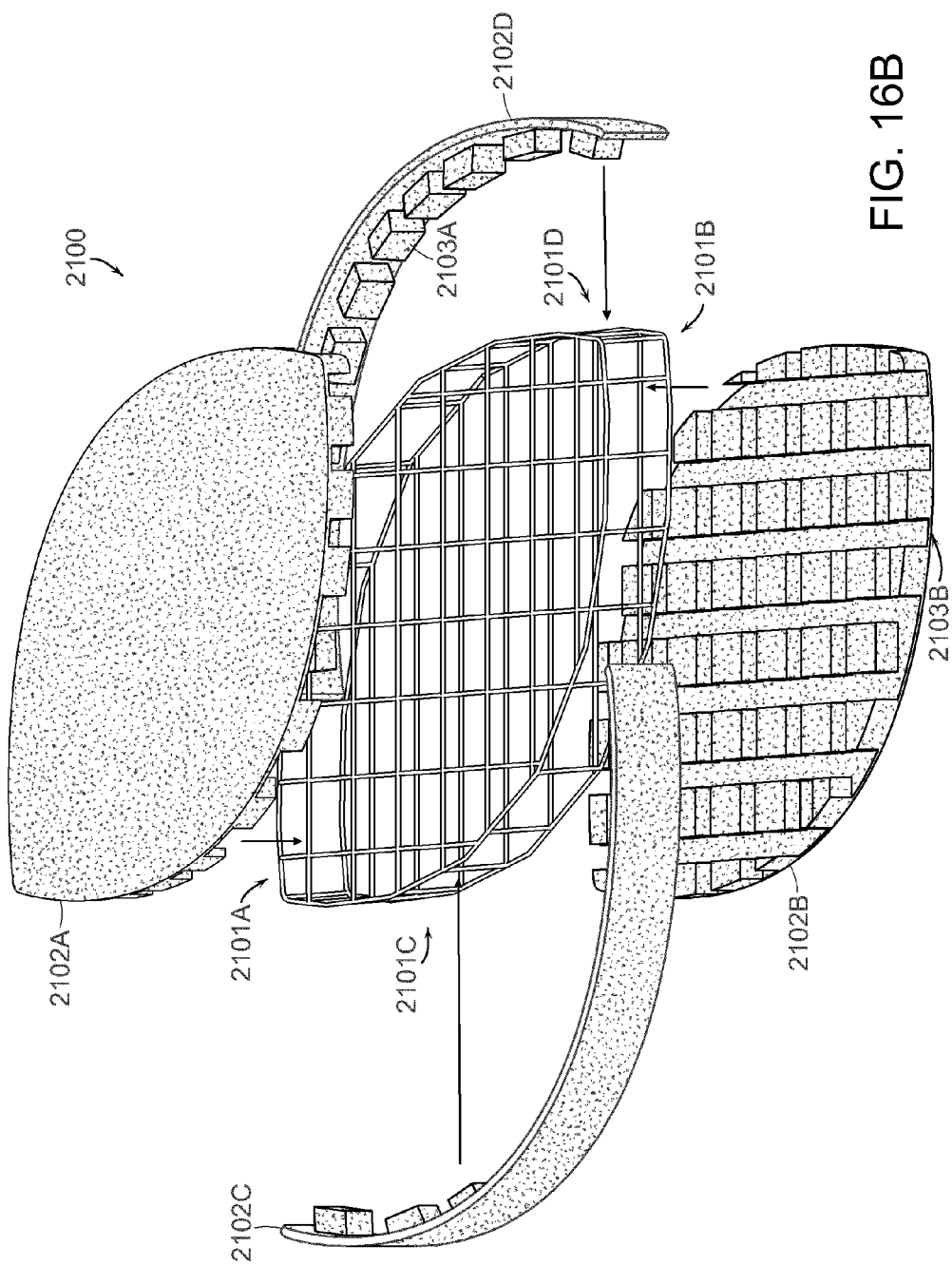
Figure 17:
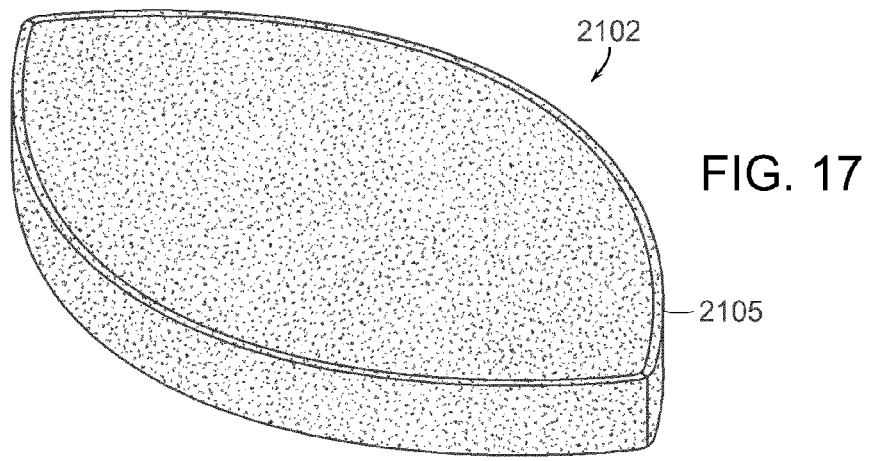
FIG. 17 shows a perspective view of the assembled device of FIG. 16B.

FIG. 16B depicts a pull apart view of the exemplary wound closure device 2100 of FIG. 16A. The exemplary device 2102 advantageously includes a stabilizing structure 2101, e.g., an endoskeleton structure such as described above, and a collapsible filler material 2102, e.g., foam or other filler material as described herein, over the stabilizing structure 2101. As depicted the filler material 2102 includes a plurality of sections of 2102A-D, configured for association with (e.g., sized and shaped to match) each of a top surface 2101A, a bottom surface 2101B, a first side surface 2101C and a second side surface 2101D of the stabilizing structure or moveable frame 2101. Thus, the sections 2102A-D of the filler material 2102 cooperate to surround the stabilizing structure 2101, e.g., forming a shell around the stabilizing structure 2101, such as depicted in FIG. 17. The device can have a covering layer 2105 that is used to contact at least the wound margins so that the layer extends around the external surface of the filler 2102. In exemplary embodiments, the stabilizing structure 2101 and the sections 2102A-D of the filler material 2102 may be configured to define a cavity for facilitating application of a negative pressure to device 2100, e.g., using negative pressure source 2120.

In some embodiments, each section 2102A, 2102B, 2102C or 2102D of the filler material 2102 can define a plurality of surface features 2103 on the inner peripheral surface thereof. For example, each of the depicted sections 2102A, 2102B, 2102C or 2102D of compressible material 2102 defines an "egg crate" pattern of protrusions 2103A and 2103B valleys. Advantageously, the surface features 2103 defined on the inner peripheral surface of the sections 2102A-D of the filler material 2102 may be configured for operative association with an inner volume of stabilizing structure 2101.

As described in previous sections, each surface 2101A, 2101B, 2101C or 2101D of the stabilizing structure 2101 may define a lattice pattern of structural elements including frame or stabilizer elements in the x-y plane (such as stabilizer elements 2108 of FIGS. 1A-1F) and stabilizer elements in the z axis (such as stabilizer elements 2110 of FIGS. 1A-1F). Thus, the surface features 2103 defined on the inner peripheral surface of each section 2102A, 2102B, 2102C or 2102D of the filler material 2102 may be configured, e.g., patterned, to match the lattice pattern of the corresponding surface 2101A, 2101B, 2101C or 2101D of the structural element 2101. For example, as depicted in FIG. 16, the surface features 2103 defined on the inner peripheral surface of the top and bottom sections 2102A and 2102B are configured such that the valleys 2103B correspond to the stabilizer elements in the x-y plane. Similarly, the surface features 2103 defined on the inner peripheral surface of the first and second side sections 2102C and 2102D are configured such that the valleys 2103B correspond to the stabilizer elements in the z axis. Thus the protrusions 2103A or pattern elements extend into an inner volume of the structural element 2101, thereby providing tensile forces to the stabilizing structure 2101, e.g., during the collapse thereof. In exemplary embodiments, the filler material 2101 may be configured to provide a pre-stress to the stabilizing structure 2101.

Figure 18A:
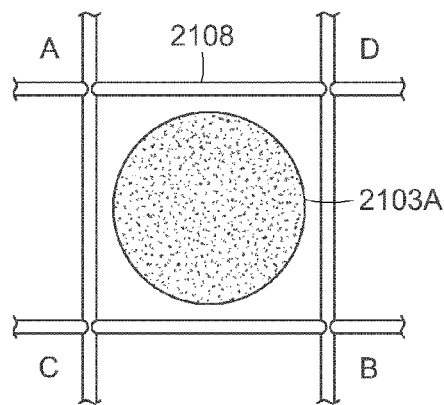
FIGS. 18A and 18B show discrete shaped elements of the wound filler within the associated structure.
Figure 18B:
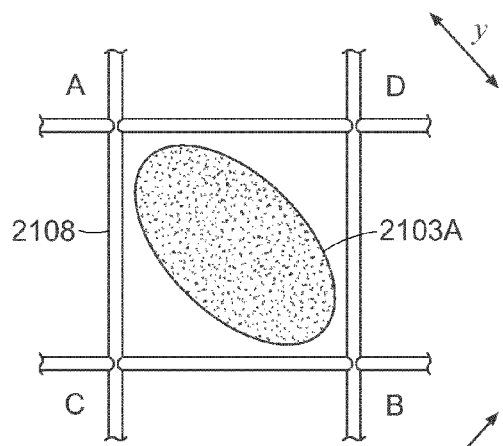

In some embodiments, the tensile forces applied by protrusions 2103a may facilitate a structured collapse of the structural element 2101, e.g., in one or more directions. For example, the surface features 2103 defined on the inner peripheral surface of each section 2102A, 2102B, 2102C or 2102D of the filler material 2102 may be configured to impart a pre-selected force profile to the stabilizing structure 2101, e.g., during the collapse thereof. In some embodiments, the pre-selected force profile may control the collapse of the structural element 2101, e.g., providing for a non-uniform collapse of filler material such as by resisting collapse in one or more directions and/or in one or more regions. With reference to FIGS. 18A-18B, different force profile configurations for individual protrusions or elements 2103A are depicted. In FIG. 18A the protrusion 2103A is configured to resist compression of the associated stabilizer elements 2108 of the structural element 2101 in both x and y directions. Thus, the protrusion is configured to provide uniform tensile forces to the stabilizing structure 2101, e.g., during the collapse thereof, in both the x and y axis. In FIG. 18B, the protrusion 2103A is configured to provide greater compression resistance of the associated stabilizer elements 2108 of the structural element in the y direction than in the x direction. Thus, the protrusion is configured to provide greater tensile forces to the stabilizing structure 2101, e.g., during the collapse thereof, in the y axis than in the x axis. In FIG. 18C a smaller protrusion 2103A is used to provide a delayed or a lower resistance to compression relative to the larger protrusion 2103A. The pattern elements from adjacent regions within the frame preferably contact each other to facilitate fluid flow under negative pressure. Thus, some regions of the stabilizing structure 2101 can be configured to collapse earlier or quicker than other regions while maintaining fluid flow.

Figure 19:
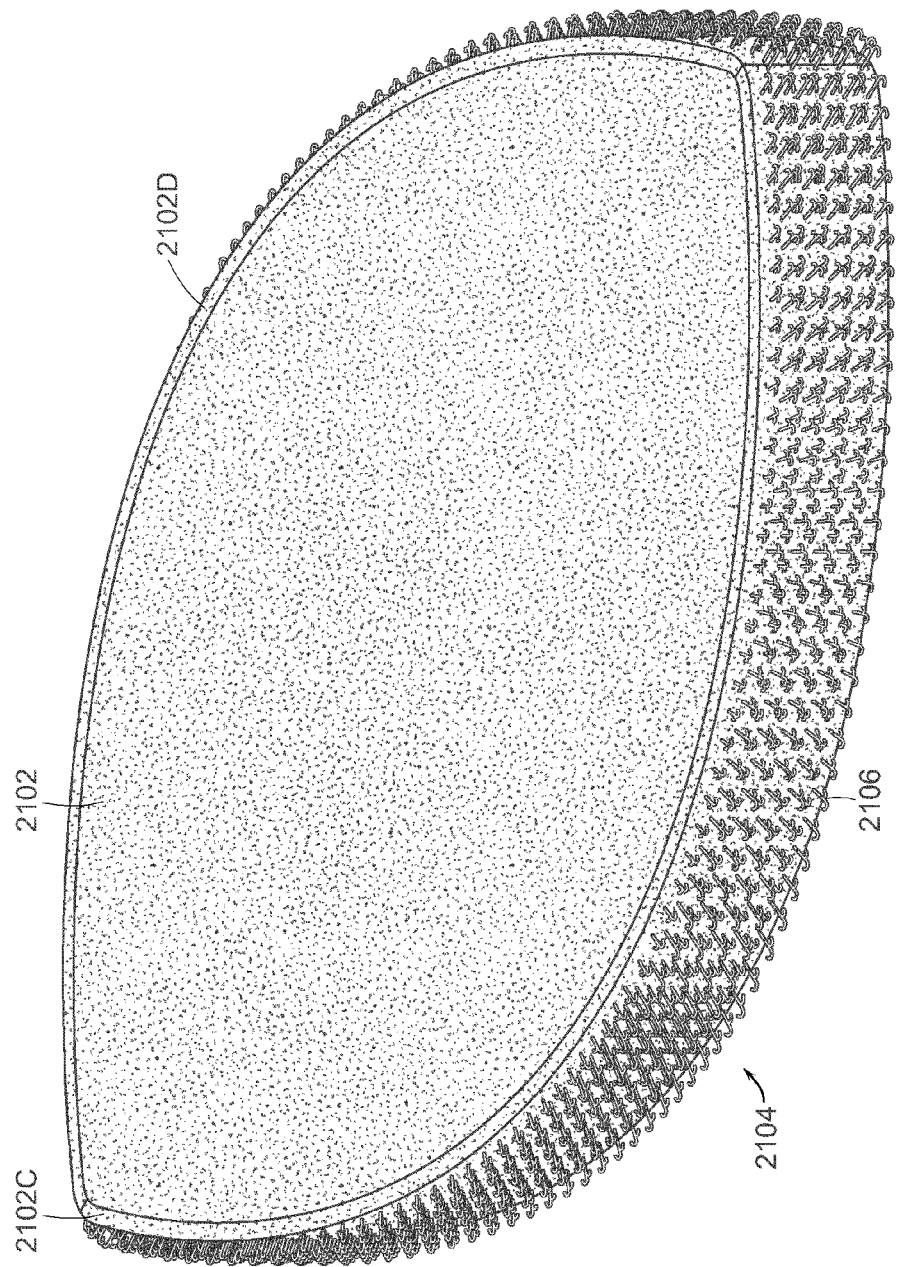
FIG. 19 illustrates an outer layer with tissue anchor elements.
Figure 20A:
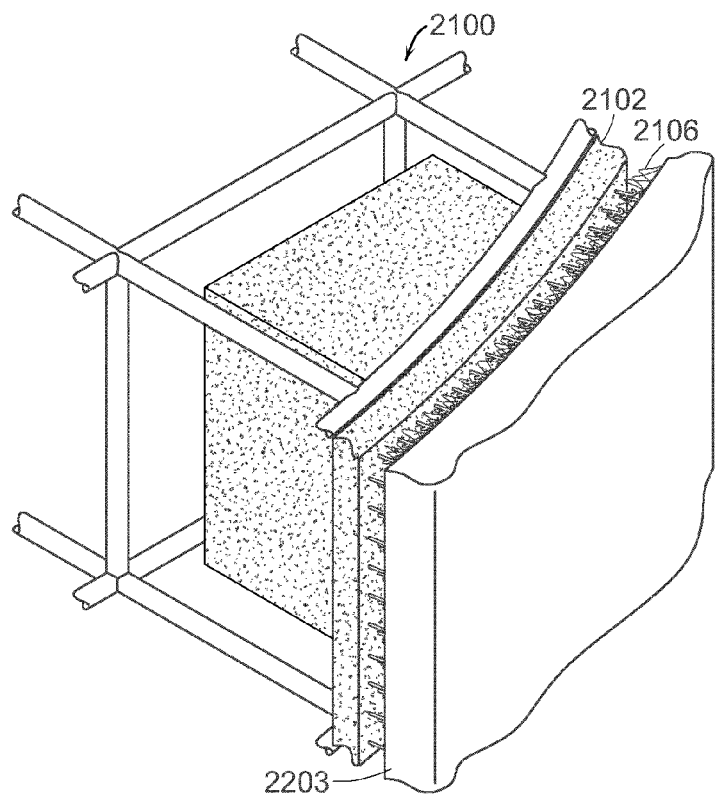
FIGS. 20A and 20B show the anchor elements adhering to tissue.
Figure 20B:
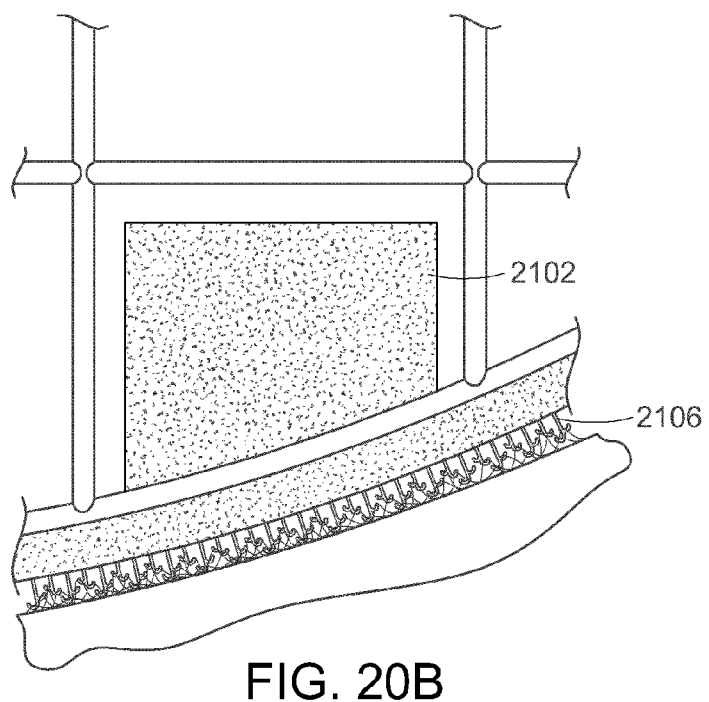

With reference to FIG. 19, exemplary embodiments, side sections 2102C and 2102D of the filler material 2102 may include a tissue grasping surface 2104, such as tissue grasping surface 2104 of FIGS. 1A-1F, extending over an outer peripheral surface of the wound filler material 2102. Note alternatively, that a separate covering layer of material such as a film or mesh as described previously can extend around the outer surfaces of the wound filler. This layer can also include tissue anchors in a further preferred embodiment as described herein such that the device can adhere to the wound margins. Tissue grasping surface 2104 may be an integral part of the filler material or may be a separate layer, e.g., secured to the filler material 2102 using any suitable technique. In exemplary embodiments, grasping surface 2104 may include a plurality of tissue anchor elements 2106 configured to engage the tissue at a wound margin. Thus, with reference to FIG. 20A, when the filler material 2102 is placed within a wound 2200, the anchor elements 2106 become buried within the tissue at the wound margins 2203 and secure the device 2100 within the wound opening 2201. As the filler material 2102 contracts, the tissue grasping surface 2104 grabs and pulls on the adjacent tissue, which is preferably the tissue around the wound margins 2203, resulting in the displacement of the tissue thereby facilitating the closure of the wound.

While the invention has been described in connection with specific methods and apparatus, those skilled in the art will recognize other equivalents to the specific embodiments herein. It is to be understood that the description is by way of example and not as a limitation to the scope of the invention and these equivalents are intended to be encompassed by the claims set forth below.

What is claimed is:

1. A negative pressure wound closure device, comprising:
   a wound filler material that is configured to be positioned within a wound opening such that the wound filler material preferentially contracts along at least a first direction relative to a second direction upon application of a negative pressure to the wound filler material; and
   a pad configured to be positioned beneath the wound filler material, the pad configured to extend outward beyond an outer perimeter of the wound filler material and configured to be positioned beneath a fascia layer.

2. The wound closure device of claim 1 further comprising a tissue anchor device that attaches the moveable structure to a wound margin of the wound opening.

3. The wound closure device of claim 1 further comprising a tissue grasping surface extending over an outer peripheral surface of the wound filler material and comprising a plurality of outward-projecting tissue anchors that contact tissue at a margin of the wound opening and displace the tissue at the wound margin upon application of the negative pressure to the filler material to facilitate closure of the wound.

4. The wound closure device of claim 1, wherein the wound filler material comprises a porous material.

5. The wound closure device of claim 1, wherein the wound filler material comprises a foam.

6. The wound closure device of claim 1, wherein tissue anchors are integrally formed in the wound filler material.

7. The wound closure device of claim 1, further comprising a layer that is provided about a surface of the filler material.

8. The wound closure device of claim 7, wherein the layer comprises a mesh material.

9. The wound closure device of claim 7, wherein the layer includes a plurality of anchors.

10. The wound closure device of claim 1, wherein the moveable structure comprises one or more regions of rigid material surrounded by regions of compressible material.

11. The wound closure device of claim 1, wherein the structure comprises a frame of flexure elements positioned over the fluid drain device, and further comprising a pad positioned under the fluid drain device that provides for lateral movement of fascia tissue overlying the pad.

12. The wound closure device of claim 11, wherein the frame comprises a plurality of spaced-apart interconnected flexure elements that bend to collapse in one direction.

13. The wound closure device of claim 11, wherein the filler material has length, width and height dimensions, and the endoskeleton enables the filler material to collapse in the width dimension and elongate in the length dimension.

14. The wound closure device of claim 1, further comprising a smooth surface extending over a bottom surface of the wound filler material.

15. The wound closure device of claim 1, wherein the filler material includes removable portions to adjust the size of the wound closure device.

16. The wound closure device of claim 2, further comprising a sensor that measures lateral force applied to tissue by a tissue anchor.

17. A method of closing a wound, comprising:
- inserting a wound closure device relative to a wound opening, the wound closure device comprising a collapsible filler material;
- extending a pad outward beyond an outer perimeter of the collapsible wound filler, the pad positioned beneath a fascia layer; and
- applying a negative pressure to the wound closure device to collapse the filler material and displace the tissue at a wound margin to facilitate closure of the wound.

18. The method of claim 17, further comprising activating a negative pressure source coupled to the wound closure device to apply the negative pressure.

19. The method of claim 17, wherein the filler material comprises a porous material.

20. The method of claim 17, further comprising securing a film over a surface of the filler material, a plurality of tissue anchors projecting outward from the film.

21. A negative pressure wound closure device, comprising:
- a wound filler material that is configured to be positioned within a wound opening such that the wound filler material preferentially contracts along at least a first direction relative to a second direction upon application of a negative pressure to the wound filler material;
- a sensor system mounted to the wound filler material configured to measure an amount of force exerted on a tissue; and
- wherein the sensor system is configured to measure an amount of force on tissue located around the peripheral wall of the wound opening.

22. A negative pressure wound closure device, comprising:
- a wound filler material that is configured to be positioned within a wound opening such that the wound filler material preferentially contracts along at least a first direction relative to a second direction upon application of a negative pressure to the wound filler material;
- a sensor system mounted to the wound filler material configured to measure an amount of force exerted on a tissue; and
- wherein the sensor system is configured to measure the amount of lateral force exerted on the tissue.

23. A negative pressure wound closure device, comprising:
- a wound filler material that is configured to be positioned within a wound opening such that the wound filler material preferentially contracts along at least a first direction relative to a second direction upon application of a negative pressure to the wound filler material;
- a sensor system mounted to the wound filler material configured to measure an amount of force exerted on a tissue;
- a tissue anchor configured to attach the wound filler material to a wound margin of the wound opening; and
- wherein the sensor system comprises a sensor that measures lateral force applied to tissue by the tissue anchor.

* * * * *